United States Patent
Brouillette et al.

(12)

(10) Patent No.: US 6,172,112 B1
(45) Date of Patent: Jan. 9, 2001

(54) RETINOIDS AND USE THEREOF

(75) Inventors: Wayne J. Brouillette, Pelham; Donald D. Muccio, Hoover, both of AL (US)

(73) Assignee: UAB Research Foundation, Birmingham, AL (US)

( * ) Notice: Under 35 U.S.C. 154(b), the term of this patent shall be extended for 0 days.

(21) Appl. No.: 09/287,705

(22) Filed: Apr. 6, 1999

Related U.S. Application Data

(60) Provisional application No. 60/080,868, filed on Apr. 6, 1998, now abandoned.

(51) Int. Cl.[7] .......................... A01N 37/06; C07C 63/06; C07C 63/64
(52) U.S. Cl. .......................... 514/559; 514/563; 562/435; 562/455; 562/469; 562/492; 562/510
(58) Field of Search .................................. 562/510, 435, 562/455, 469, 492; 514/559, 563

(56) References Cited

U.S. PATENT DOCUMENTS 5,094,783 * 3/1992 Muccio et al. ...................... 260/413

OTHER PUBLICATIONS

Database CAPLUS on STN, Acc. No. 1996:513748, Muccio et al., 'Conformationally defined 6–s–trans retinoic acid analogs 3. Structure–activity relationships for nuclear receptor binding, transcriptional activity and cancer chemopreventive activity.' J. Med. Chem. (1996), 39(19), pp. 3625–3635 (abstract).*

* cited by examiner

*Primary Examiner*—Paul J. Killos
*Assistant Examiner*—Brian J. Davis
(74) *Attorney, Agent, or Firm*—Benjamin Aaron Adler

(57) ABSTRACT

The present invention provides new retinoid compounds and uses of the compounds in humans and animals for chemoprevention of skin and/or breast cancer and for therapy of leukemia.

26 Claims, 15 Drawing Sheets

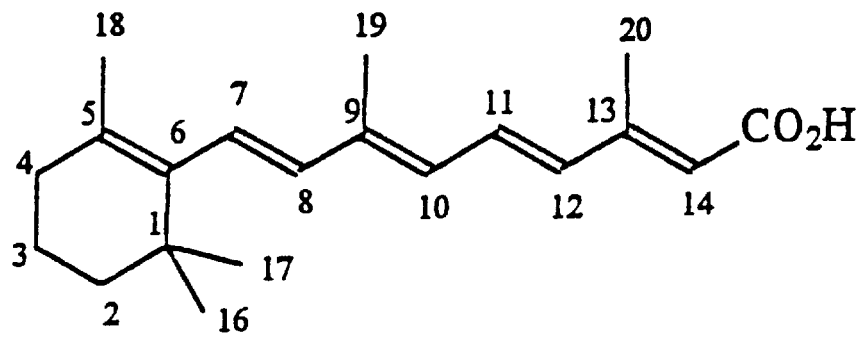
All-trans-retinoic acid
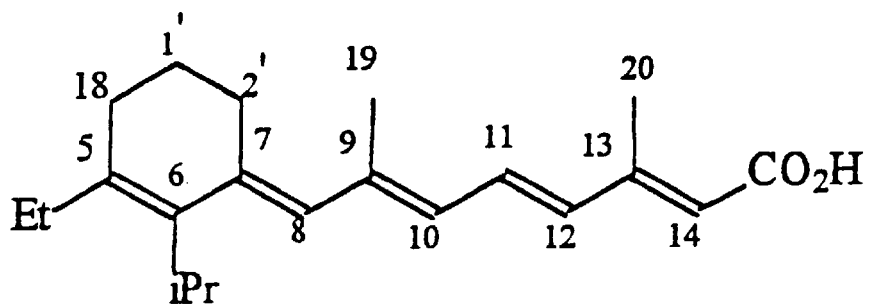
All-trans-UAB8
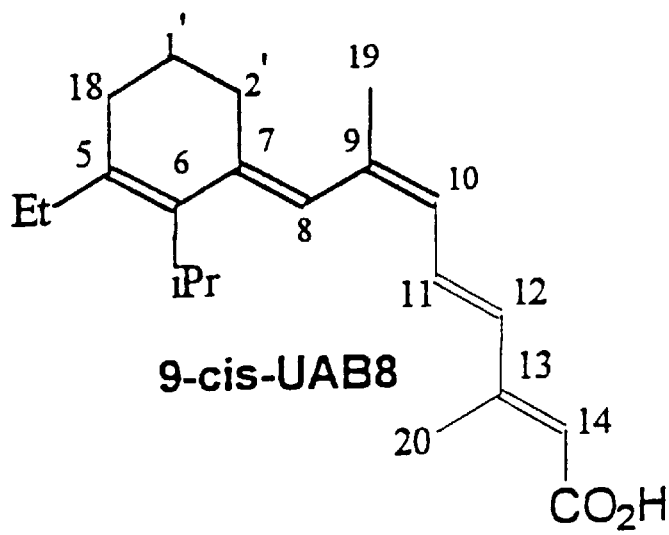
9-cis-UAB8
FIG. 4-1

All-trans-UAB30

9-cis-UAB30

RETINOIDS AND USE THEREOF

CROSS-REFERENCE TO RELATED APPLICATION

This patent application claims benefit of provisional patent application U.S. Serial No. 60/080,868, filed Apr. 6, 1998, now abandoned.

FEDERAL FUNDING LEGEND

This invention was created in part using funds supplied by the United States government under grant PO1 CA34968. Consequently, the United States government has certain rights in this invention.

BACKGROUND OF THE INVENTION

1. Field of the Invention

The present invention relates generally to the fields of chemistry and cancer treatment. More specifically, the present invention relates to novel retinoids and their use in chemoprevention and cancer therapy.

2. Description of the Related Art

In chemical descriptions that follow, E may be interchanged synonymously with trans, and Z may be interchanged synonymously with cis.

Retinoid receptors and other this superfamily of nuclear receptors (that include the steroid, thyroid and vitamin D hormone receptors and other "orphan" receptors without known ligands) are new targets for drug development (1). It is thought that retinoic acid (RA) and synthetic retinoids act a s ligand-dependent transcription factors with different members of nuclear retinoid receptors to control gene transcription responsible for cellular proliferation, differentiation, development and cell death (2). Two classes of nuclear retinoid receptors (RARs and RXRs) have been identified so far, and each has several different subtypes ($\alpha$, $\beta$, $\gamma$). Both (all-E)- and (9Z)-RA bind to RARs and activate transcription mediated by RAR/RXR heterodimers, but (9Z)-RA is the only known natural ligand for the RXRs which mediate transcription by forming homodimers or heterodimers.

Recent advances in chemoprevention have heightened interest in the use of retinoids in several types of solid organ tumors, and major therapeutic successes have been demonstrated with retinoids in certain leukemias (3). (all-E)-RA treatment of patients with acute promyelocytic leukemia (APL) leads to a 90% complete remission rate in these patients by inducing normal maturation and apoptosis of APL myeloblasts to neutrophils, but this differentiation therapy is transient and is commonly followed by relapse within 3–15 months, probably due to the development of resistance to retinoic acid (4). (13Z)-RA effectively controls the excessive myeloproliferation in up to 50% of children with juvenile myelomonocytic leukemia (JMML) (5). However, this treatment is not curative and at best can lead to a period of prolonged stabilization of disease, but ultimately patients need to undergo allogenic bone marrow transplantation (4, 6).

All-trans-retinoic acid (ATRA) is the first example of a FDA-approved agent used for differentiation therapy (rather than standard cytotoxic cancer chemotherapy) of patients with APL. Even though it has been shown to be highly effective in APL treatment, clinical resistance occurs frequently with pharmacological doses of ATRA and APL patients often relapse (Degos et al., 1995, *Blood*, 85, 2643). In order to provide more effective therapies, new highly active retinoids need to be identified in the expectation that lower doses of these agents would not induce relapse as rapidly as ATRA.

The NB4 cell line, which was isolated from an APL patient undergoing ATRA therapy, offers an excellent in vitro model of APL. The t(15;17) translocation, which is characteristic of APL, is stably carried in NB4 cells, and the PML/RAR-a fusion protein is expressed in this transformed cell line (Lanotte et al, 1991, Blood, 77:1080). ATRA treatment of NB4 cells remove the PML/RAR-a block to differentiation and allow the promyelocytes to mature normally and die. The mechanism by which ATRA removes the differentiation block is not well understood. Recent evidence suggests that ATRA downregulates the expression of PML/RAR-a and restores the normal myeloid differentiation (Raelson et al., 1996 Blood, 88, 2826).

The prior art is deficient in effective therapeutic agents with the beneficial effects of retinoic acid but which have reduced side effects. The present invention fulfills this long-standing need and desire in the art.

SUMMARY OF THE INVENTION

The present invention demonstrates that UAB8 isomers have equal or greater efficacy as compared to the isomers of natural retinoic acid. Also provided is a new retinoid, UAB30, whose all-E-isomer has different nuclear receptor selectivity (RAR$\beta$ and RAR$\gamma$ subtype-selective retinoid and RAR$\alpha$ antagonist) than (all-E)-UAB8.

The present invention also evaluates new conformationally constrained retinoids, named UAB retinoids, in NB4 cell differentiation assays and identified all-trans-UAB8 with more potency than ATRA (Muccio et al., 1998 *J. Med. Chem.*, 41, 1679). In order to further evaluate its potential in APL therapy, its ability to induce NB4 cell differentiation was studied in the presence of RXR-selective retinoids, which have been shown to enhance ATRA effectiveness (Chen et al., 1996, Nature, 382, 819). Further, UAB retinoids that dissociate the RAR-$\alpha$ transactivation and transrepression actions of ATRA were identified and used to understand the RAR-mediated mechanisms of all-trans-UAB8 in NB4 cell differentiation.

In one embodiment of the present invention, there are provided compounds for a new structural class of retinoids. These compounds are analogs of UAB8 illustrated by general structures I and II. Representative examples are (9Z)-UAB20, (all E)-UAB20, (9Z)-UAB21 and (all E)-UAB21.

In another embodiment of the present invention, there are provided compounds for another new structural class of retinoids, wherein the compounds are UAB30 and analogs. Representative examples are (9Z)-UAB30, (9Z)-UAB31, (9Z)-UAB32, (9Z)-UAB33, (all E)-UAB33, (9Z)-UAB34, (9Z)-UAB35, (9Z)-UAB60, (9Z)-UAB61, (9Z)-UAB62, (9Z)-UAB40 and (9Z)-UAB70.

In still another embodiment of the present invention, there is provided a method of treating an individual in need of such treatment by administering to the individual an effective dose of the new retinoid compound. Preferably, the individual is in need of treatment for leukemia or in need of cancer chemoprevention. The retinoid compounds can be used synergistically for the treatment.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
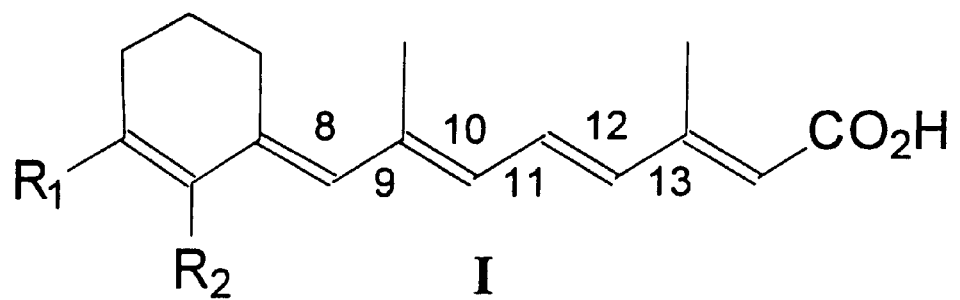
FIG. 1 shows general structures I and II, which describe UAB8 and analogs (UAB8 is defined as $R_1$=ethyl and $R_2$=i-propyl in structure I), wherein $R_1$ is selected from the group consisting of H, ethyl, methyl, n-propyl, i-propyl, t-butyl, phenyl, benzyl, cyclic alkyl (from C3–C8), aryl, and arylalkyl; and $R_2$ is selected from the group consisting of 2-methylpropyl, n-butyl, cyclohexyl, 3-cyclohexenyl, benzyl, cyclic alkyl (from C3–C8), and arylalkyl. And wherein $R_1$ is selected from the group consisting of phenyl, benzyl, cyclic alkyl (from C3–C8), aryl, and arylalkyl; and $R_2$ is selected from the group consisting of H, ethyl, methyl, n-propyl, and i-propyl.
Figure 1:
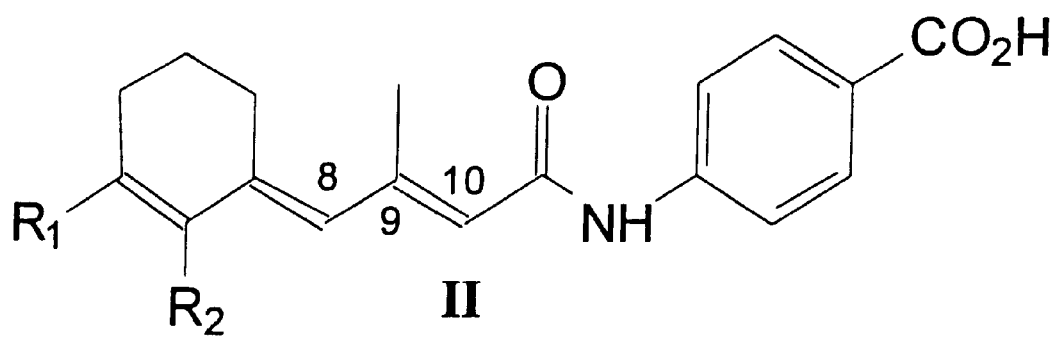

The present invention is directed to new retinoid compounds and their uses. All-trans-retinoic acid (ATRA) induces the acute promyelocytic leukemia (APL) cell line, NB4, to terminally differentiate to granulocytes. Clinically, ATRA is used as an alternative therapy for APL patients who become refractive to normal cytotoxic chemotherapy. However, most APL patients develop clinical resistance with prolonged ATRA therapy. All-trans-UAB8 is identified as a more effective agent than ATRA in inducing NB4 cells to differentiate. The present invention also investigates the effects of all-trans-UAB8, a RAR-selective retinoid, in NB4 cell differentiation when used in combination with 9-cis-UAB8 or 9-cis-UAB30, two RXR-selective retinoids. The combined use of all-trans-UAB8 and 9-cis-UAB30 acted synergistically in NB4 cell differentiation, while 9-cis-UAB30 had little effect alone. Additionally, all-trans-UAB8 and 4-hydroxyphenylretinamide acted synergistically to induce NB4 cells to differentiate.

Potential nuclear receptor-based mechanisms of action of retinoid-induced differentiation in this cell line was next explored. All-trans-UAB8 was demonstrated to be very effective in both RAR-mediated transactivation of genes and in RAR-mediated transrepression of the AP-1 complex (c-Jun/c-Fos). To distinguish between these two receptor-based mechanisms, all-trans-UAB30 was evaluated and was active in transrepression of AP-1 complex, but as a RAR-α antagonist. When used alone, all-trans-UAB30 did not induce differentiation of NB4 cells, and, when used in combination, it reduced the effectiveness of either all-trans-UAB8 or ATRA. These data support a RAR-α-based mechanism of all-trans-UAB8 induced differentiation of NB4 cells. Finally, all-trans-UAB8 was found to be metabolized at the same rate as ATRA, but that 9-cis-UAB30 was metabolically stable for 5 days. Taken together, the present invention discloses that the effectiveness of all-trans-UAB8 can be further increased when used in combination with metabolically stable RXR-selective ligands, providing a new combination therapy for the clinical treatment of APL.

In one embodiment of the present invention, there are provided retinoid compounds that are analogs of UAB8 (UAB8 is defined as $R_1$=ethyl and $R_2$=i-propyl in structure I) having the structure selected from the group consisting of structure I and structure II:

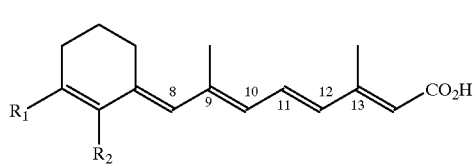

I

-continued

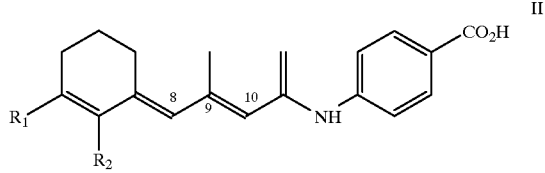
II wherein $R_1$ is selected from the group consisting of H, ethyl, methyl, n-propyl, i-propyl, t-butyl, phenyl, benzyl, cyclic alkyl (from C3–C8), aryl, and arylalkyl; and $R_2$ is selected from the group consisting of 2-methylpropyl, n-butyl, cyclohexyl, 3-cyclohexenyl, benzyl, cyclic alkyl (from C3–C8), and arylalkyl and wherein $R_1$ is selected from the group consisting of phenyl, benzyl, cyclic alkyl (from C3–C8), aryl, and arylalkyl; and $R_2$ is selected from the group consisting of H, ethyl, methyl, n-propyl, and i-propyl.

Preferably, the retinoid compounds that are analogs of UAB8 are selected from the group consisting of (9Z)-UAB20, (all E)-UAB20, (9Z)-UAB21 and (all E)-UAB21, wherein (9Z)-UAB20, (all E)-UAB20, (9Z)-UAB21 and (all E)-UAB21 having the structure:

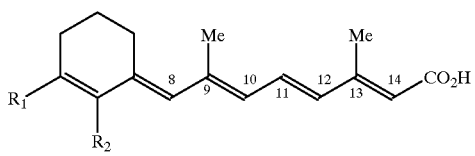

wherein (9Z)-UAB20 and (all E)-UAB20 have a Ph group as $R_1$ and an i-propyl group as $R_2$; wherein (9Z)-UAB21 and (all E)-UAB21 have $CH_2CH(CH_3)_2$ as $R_1$ and an i-propyl group as $R_2$.

In another embodiment of the present invention, there are provided retinoid compounds, i.e., UAB30 and analogs, having the structure selected from the group consisting of structures III and structure IV:

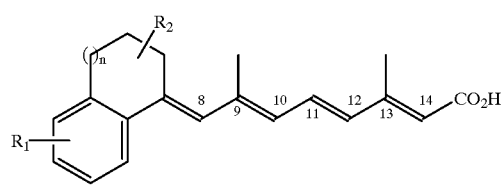
III

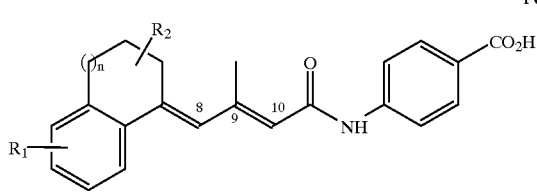
IV wherein $R_1$ represents one or two substituents on the aryl ring and is selected from the group consisting of H, ethyl, methyl, n-propyl, i-propyl, t-butyl, phenyl, benzyl, chloro, fluoro, methoxy, ethoxy, benzyloxy, cyclic alkyl (from C3–C8), aryl, arylalkyl, alkyloxy, aryloxy, arylalkyloxy, and halogen; $R_2$ is selected from the group consisting of H, ethyl, methyl, n-propyl, i-propyl, 2-methylpropyl, n-butyl, cyclohexyl, 3-cyclohexenyl, benzyl, methoxy, ethoxy, benzyloxy, cyclic alkyl (from C3–C8), aryl, arylalkyl, alkyloxy, aryloxy and arylalkyloxy; and wherein n=0–3.

Preferably, the retinoid compounds UAB30 and analogs are selected from the group consisting of (9Z)-UAB30, (9Z)-UAB31, (9Z)-UAB32, (9Z)-UAB33, (all E)-UAB33, (9Z)-UAB34, (9Z)-UAB35, (9Z)-UAB60, (9Z)-UAB61 and (9Z)-UAB62, wherein (9Z)-UAB30, (9Z)-UAB31, (9Z)-UAB32, (9Z)-UAB33, (all E)-UAB33, (9Z)-UAB34, and (9Z)-UAB35 having the structure:

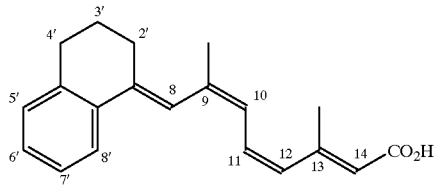

wherein (9Z)-UAB30 having an substituent H on the aryl ring; (9Z)-UAB31 having an substituent 5'-methoxy on the aryl ring; (9Z)-UAB32 having an substituent 6'-methoxy on the aryl ring; (9Z)-UAB33 having an substituent 7'-methoxy on the aryl ring; (all E)-UAB33 having an substituent 7'-methoxy on the aryl ring; (9Z)-UAB34 having an substituent 4'-methyl on the cycloalkyl ring; and (9Z)-UAB35 having two substituents 5',7'-dimethyl on the aryl ring;

wherein (9Z)-UAB60, (9Z)-UAB61 and (9Z)-UAB62 having the structure:

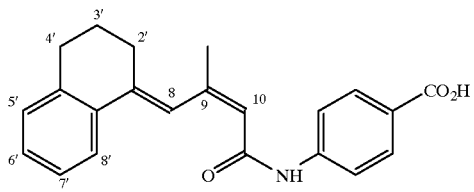

wherein (9Z)-UAB60 has an substituent H on the aryl ring; (9Z)-UAB61 has an substituent 5'-methoxy on the aryl ring; and (9Z)-UAB62 has an substituent 7'-methoxy on the aryl ring.

More preferably, (9Z)-UAB40 having the structure:

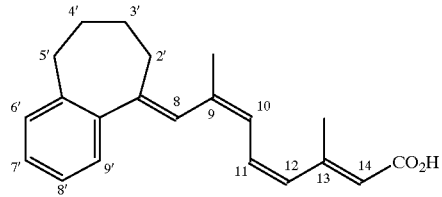

and (9Z)-UAB70 having the structure:

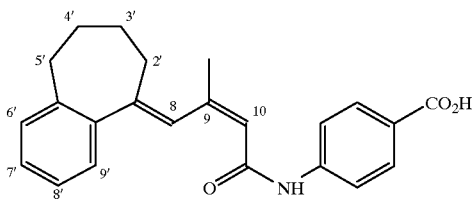

are representative examples of UAB30 and analogs.

In still another embodiment, the present invention is directed to methods of treating an individual having a neoplastic condition or suspected of having a neoplastic or neoplastic-like condition by administering to the individual an effective dose of the retinoid compound disclosed herein. Preferably, the retinoid compound is further combined with 4-hydroxyphenylretinamide for the treatment. More preferably, the individual is in need of treatment for leukemia or in need of cancer chemoprevention, such as skin or breast cancer. Still preferably, the compound is administered at a dosage range of from about 10 mg/kg of body weight to about 300 mg/kg of body weight.

In still yet another embodiment of the present invention, there is provided a method of treating an individual having a neoplastic condition by administering to the individual a combination of two or more than two retinoid compounds disclosed herein. The combination may further comprise 4-hydroxyphenylretinamide. Still preferably, the individual is in need of treatment for leukemia or in need of cancer chemoprevention.

Thus, there is provided a method of treating an individual having a neoplastic condition, comprising the step of administering to said individual an effective dose of UAB8 and other compounds disclosed herein as shown in the claims below. Further, this compound can be combined with 4-hydroxyphenylretinamide. Representative neoplastic conditions which can be so treated include skin cancer, breast cancer, bladder cancer, prostate cancer, lung cancer, colon cancer, and leukemia. Preferably, the compound is administered at a dosage of from about 10 mg/kg of body weight to about 300 mg/kg of body weight.

The present invention is also directed to a method of treating an individual having a neoplastic condition, comprising the step of administering to said individual a combination of two or more than two retinoid compounds selected from the group consisting of UAB8/analogs and UAB30/analogs. The combination may further comprise 4-hydroxyphenylretinamide. Still preferably, the individual is in need of treatment for leukemia or in need of cancer chemoprevention. Representative neoplastic conditions which can be so treated include skin cancer, breast cancer, bladder cancer, prostate cancer, lung cancer, colon cancer, and leukemia. Preferably, the compound is administered at a dosage of from about 10 mg/kg of body weight to about 300 mg/kg of body weight.

The following examples are given for the purpose of illustrating various embodiments of the invention and are not meant to limit the present invention in any fashion.

EXAMPLE 1

Chemistry of Retinoic Acid Analogues $^1$H NMR spectra were obtained at 400.1 MHz (Bruker DRX spectrometer) in $CDCl_3$. NOE experiments were performed on degassed samples using 2D phase-sensitive NOESY experiments with different mixing times (between 250 and 2000 ms). Typically, 1 s mixing times were used with 16 pulses for phase cycling and 2 dummy scans. The data were processed with line broadening of 0.3 Hz in each dimension and zero-filled to yield 512×4096 2D contour plots. The integrated intensities of the negative cross-peaks were determined using standard Bruker NMR software features.

Figures 1, 3:
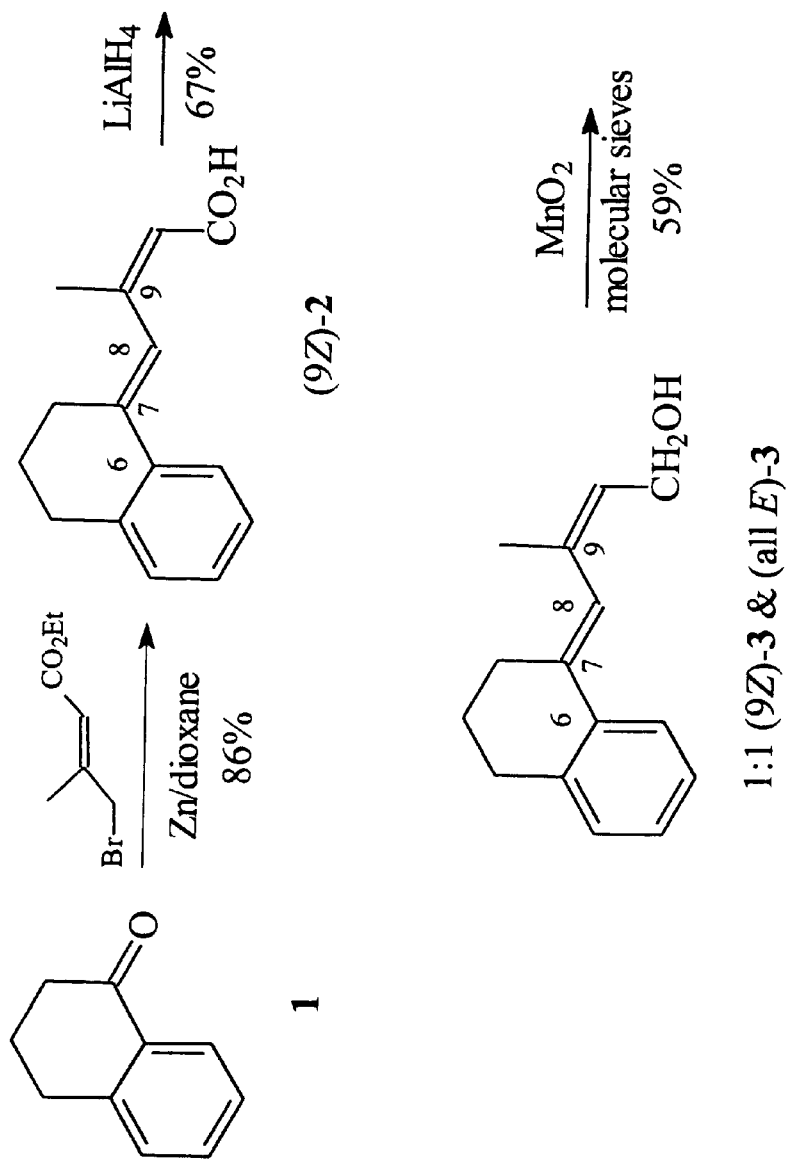
FIG. 3 shows the scheme of preparing UAB30.
Figures 2, 3:
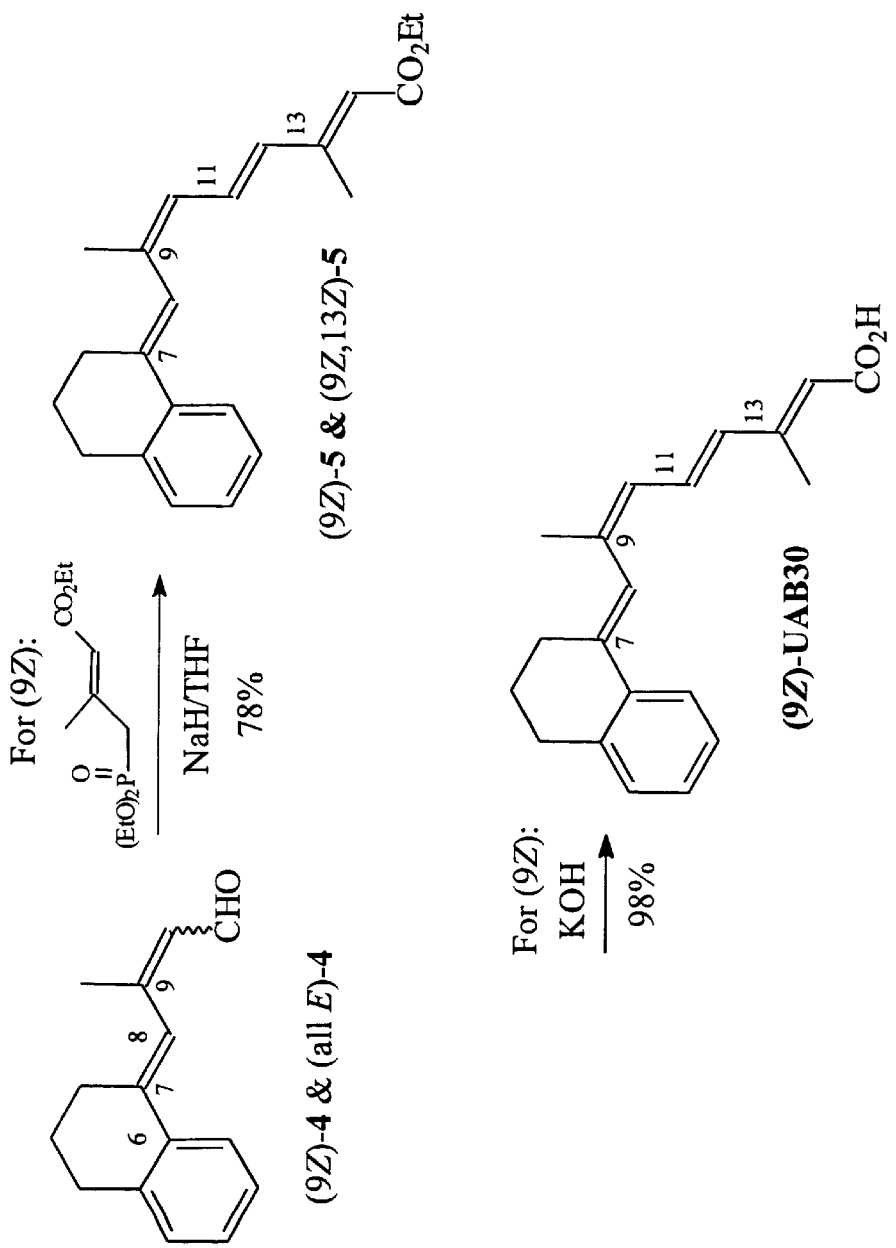
Figure 3:
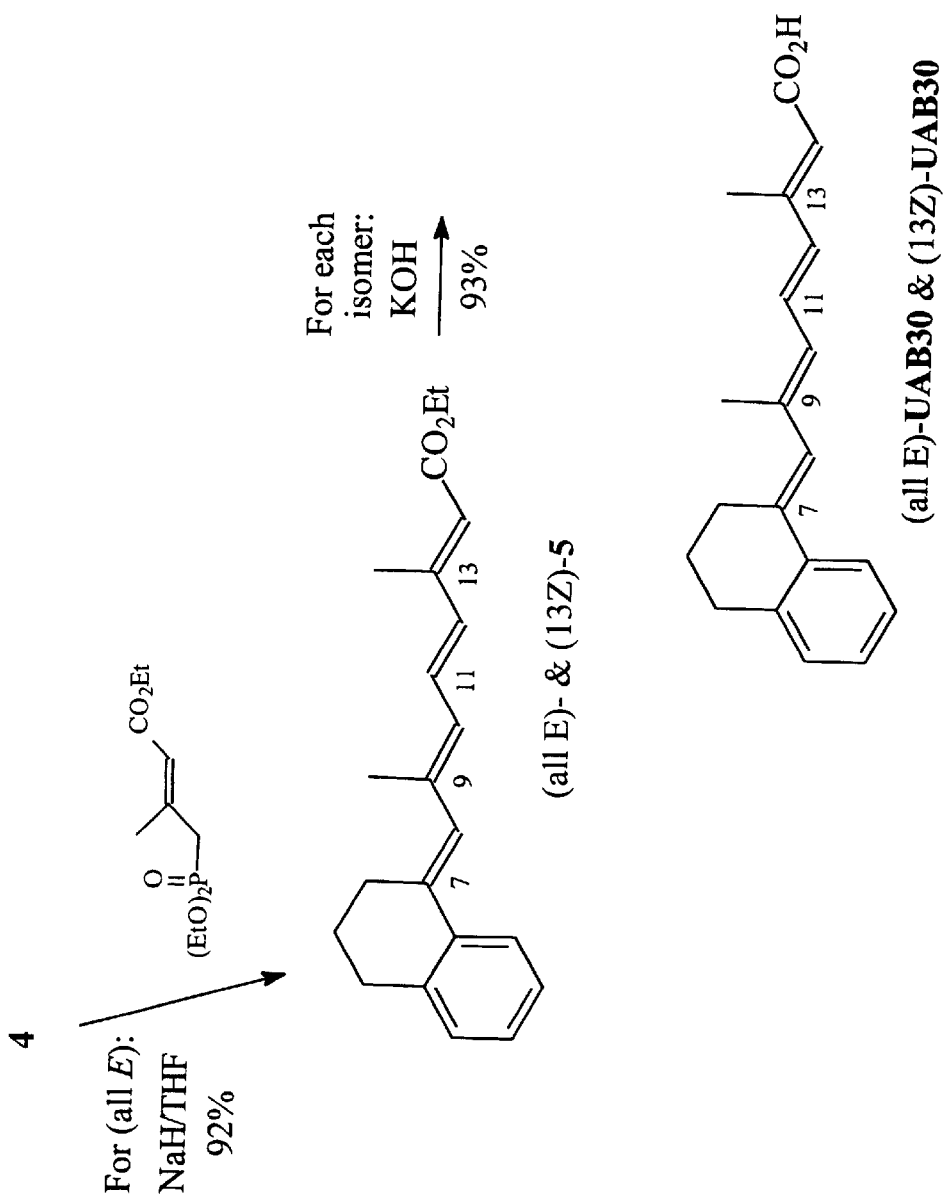
Figure 4:
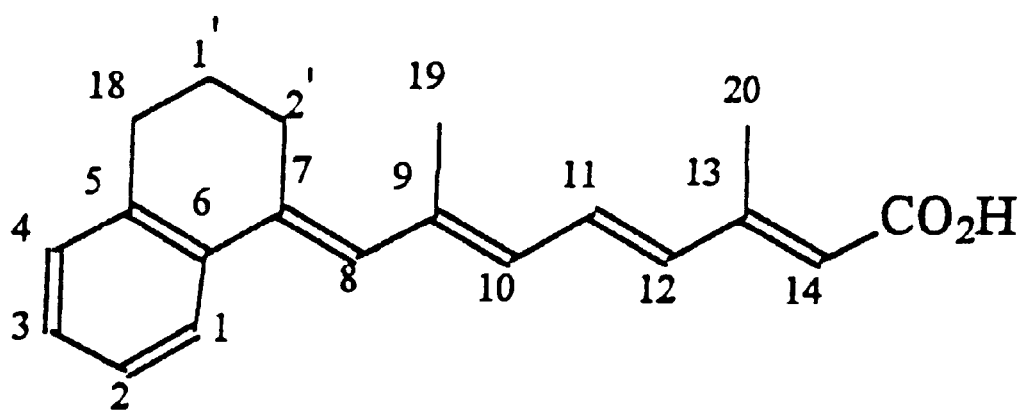
FIG. 4 shows the structures of all-trans-retinoic acid (ATRA) compared to all-trans- and 9-cis-isomers of UAB8 and UAB30 retinoids.
Figure 2:
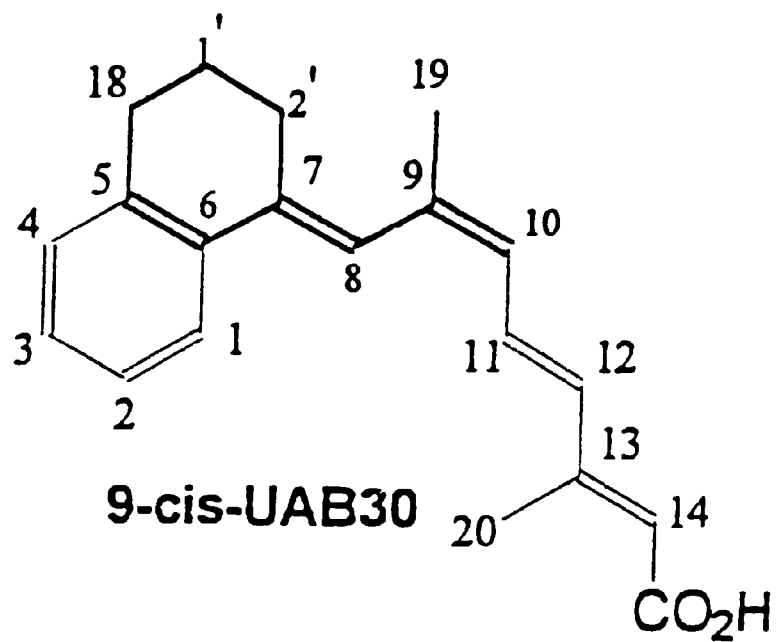

UV/vis spectra were recorded on an AVIV 14DS spectrophotometer in cyclohexane or methanol solutions (Fisher, Spectrograde). IR spectra were recorded using a Nicolet FT IR spectrometer on thin films. HPLC separations were performed on a Gilson HPLC gradient system using 25-ml pump heads and an ISCO $V^4$ variable wavelength detector. The column employed was a Whatman Partisil 10 M20/50 (500-×22-mm i.d.) with a flow rate of 5 ml/min and monitoring by UV/vis detection at 340 nm. TLC chromatography was performed on precoated 250-$\mu$m silica gel GF glass plates (Analtech, Inc.; 5×10 cm). Solvents and liquid starting materials were distilled prior to use. Reactions and purifications were conducted with deoxygenated solvents, under inert gas (N2) and subdued lighting. Selected data for the intermediates and products in the scheme shown in FIG. 3 are contained in Table 1.

(2Z,4E)-4-(3',4'-Dihydro-1'(2'H)-naphthalen-1'-ylidene)-3-methyl-2-butenoic Acid ((9Z)-2)

Zinc dust (1.75 g, 26.8 mmol) was stirred with 5% HCl (5 ml) for 2 min at room temperature. The mixture was allowed to settle, and the liquid was carefully removed by pipet. In a similar fashion the Zn was washed, under nitrogen, with water (3×5 ml), acetone (3×5 ml), and ether (2×8 ml). After residual ether was removed under a stream of nitrogen, the flask containing the Zn dust was strongly heated with a Bunsen burner flame for 30 s. The cooled Zn dust was suspended in anhydrous dioxane (3 ml), and the stirred suspension was heated to reflux. A solution of freshly distilled α-tetralone (0.520 g, 3.56 mmol), ethyl bromosenecioate (1.47 g, 7.12 mmol), and anhydrous dioxane (2.5 ml) was prepared under nitrogen, and a portion of this solution (0.5 ml) was added to the heated Zn suspension. This produced an exothermic reaction, and the remainder of the solution containing α-tetralone was then added during 10 min at a rate sufficient to control reflux. The final reaction mixture was stirred at reflux for 8 hours and then cooled to room temperature. Water (5 ml) was added, the mixture was stirred for 20 min, and ether (20 ml) was added. The suspension was filtered through a pad of Celite and the filter washed well with ether (40 ml). The filtrate was extracted with 15% HCl (40 ml), water (40 ml), 1N NaOH (40 ml), and an additional amount of water (30 ml). the basic wash and final water wash were combined, adjusted to pH 1–2 with 15% HCl, and extracted with ether (2×100 ml). The organic layer was dried ($Na_2SO_4$) and concentrated under vacuum to (9Z)-2 as yellow crystals (0.70 g, 86% yield): mp 153–154° C. (1:1 hexane-ethyl acetate).

(2Z,4E)- and (2E,4E)-4-(3',4'-Dihydro-1'(2'H)-naphthalen-1'-ylidene)-3-methyl-2-buten-1-ol ((9Z)- and (all-E)-3)

A solution of acid (9Z)-2 (0.11 g, 0.48 mmol) in anhydrous THF (10 ml) was cooled to −78° C., and 1 M $LiAlH_4$/ether (0.50 ml, 0.50 mmol) was added dropwise with stirring under nitrogen. The dry ice-acetone bath was removed, and the reaction mixture was brought to room temperature and stirred for 3 hr. The reaction mixture was cooled to 0° C., and methanol (0.2 ml) followed by 10% HCl (10 ml) was added dropwise. This was allowed to warm to room temperature, and the mixture was extracted with ether (2×20 ml). The ether layer was washed with brine (1×20 ml), dried ($Na_2SO_4$), and concentrated under vacuum to give an oily residue (0.113 g). This was placed on a flash silica gel column (1×30 cm) and eluted with 30% Et$_2$O-hexane to give a 1:1 mixture of (9E)- and (all-E)-3 (0.068 g, 67% yield). The alcohol mixture was carried on in this form without further purification.

(2Z,4E)- and (2E,4E)-4-(3',4'-Dihydro-1'(2'H)-naphthalen-1'-ylidene)-3-methyl-2-butenal ((9Z)- and (all-E)-4)

To a stirred solution of alcohol 3 (0.065 g, 0.30 mmol) in dry Ch$_2$Cl$_2$ (10 ml) at 0° C., under nitrogen, was added 4 A molecular sieves (1.5 g) followed by activated MnO$_2$ (0.53 g, 6.1 mmol), and the mixture was stirred at 0° C. for 3 hr. The reaction mixture was filtered through a pad of flash silica gel, and the filter was washed with cold 50% CH$_2$Cl$_2$/ether (100 ml). The filtrate was concentrated to dryness under vacuum to give a residual oil (0.05). This was placed on a flash silica gel column (1×15 cm) and eluted with 10% Et$_2$O-hexane to give (9Z)-4 (0.018 g), (all-E)-4 (0.016 g), and starting alcohol 3 (0.007 g). The total yield of 4 was 0.034 g (59% yield based on unrecovered starting alcohol).

General Procedure for the Olefination of Individual Isomers of Aldehyde 4

NaH (1.2 equiv.) was washed in dry THF three times to eliminate mineral oil. At 0° C. under N$_2$, freshly distilled triethyl phosphonosenecioate (1.1 equiv.) in THF was added. After the mixture stirred for 30 min, HMPA (0.2 equiv.) followed by ether (9Z)- or (all-E)-4 (1 equiv., final concentration 0.8 M) was added. After the mixture reacted for 120 min at room temperature, water was added and the reaction mixture was partitioned between ether and water. The ether layer was washed once with brine, dried (Na$_2$SO$_4$), and concentrated under vacuum to give ester as a mixture of mainly two configurational isomers. By this method were prepared the following.

(2E,4E,6Z,8E)- and (2Z,4E,6Z,8E)-Ethyl 8-(3',4'-Dihydro-1'(2'H)-naphthalen-1'-ylidene)-3,7-dimethyl-2,4,6-octatrienoate ((9Z)- and (9Z, 13Z)-5)

This preparation employed a suspension of NaH (0.060 g, 2.5 mmol) in dry THF (1 ml), a solution of triethyl phosphonosenecioate (0.14 g, 0.53 mmol) in dry THF (1 ml), HMPA (0.041 g, 0.21 mmol), and a solution of (9Z)-4 (0.089 g, 042 mmol) in dry THF (1 ml) to give a 2:1 mixture of esters (9Z)- and (9Z, 13Z)-5 (0.12 g, 78% yield). This mixture was prepared by HPLC on silica gel using 0.5% Et$_2$O, 01% THF in hexane.

(2E,4E,6E,8E)- and (2Z,4E,6E,8E)-Ethyl 8-(3',4'-Dihydro-1'(2'H)-naphthalen-1'-ylidene-3,7-dimethyl-2,4,6-octatrienoate ((all-E)- and (13Z)-5)

This preparation employed a suspension of NaH (0.050 g, 2.1 mmol) in dry THF (1 ml), a solution of triethyl phosphonoseneciaote (0.11 g, 0.40 mmol) in dry THF (1 ml), HMPA (0.048 g, 0.22 mmol), and a solution of (all-E)-4 (0.065 g, 0.31 mmol) in dry THF (1 ml) to give a 2:1 mixture of esters (all-E) and (13)-5 (0.12 g, 78% yield). This mixture was separated by HPLC on silica gel using 1% Et$_2$O, 0.5% THF in hexane.

Procedure for the Hydrolysis of Individual Isomers of Ester 5

To a solution of the ester 5 (1 equiv.) in methanol (final concentration 0.061 M) was added an aqueous solution of 2 M KOH (10 equiv.). This solution was heated at reflux, and the reaction progress was monitored by TLC. After 90 min the hot solution was poured into a beaker of ice (40 g) and acidified with 10% HCl until pH2. The mixture was then extracted with Et$_2$O, which was washed with brine, dried (Na$_2$SO$_4$), and concentrated under reduced pressure to give the product. NMR revealed that the hydrolysis occurred without isomerization. The following acids were synthesized by this method.

(2E,4E,6E,8E)-8-(3',4'-Dihydro-1'(2'H)-naphthalen-1'-ylidene)3,7-dimethyl-2,4,6-octatrienoic acid ((all-E)-UAB30)

This preparation utilized a solution of KOH (0.258 g, 4.61 mmol) in water (2 ml) and a warm solution of ester (all-E)-5 (0.122 g, 0.378 mmol) in methanol (10 ml) to provide acid (all-E)-UAB30 (0.104 g, 93% yield) as a yellow solid: mp 192–197° C. (cyclohexane).

(2E,4E,6E,8E)-8-(3',4'-Dihydro-1'(2'H)-naphthalen-1'-ylidene)3,7-dimethyl-2,4,6-octatrienoic acid ((9Z)-UAB30)

This preparation utilized a solution of KOH (0.15 g, 2.8 mmol) in water (1 ml) and a warm solution of ester (9Z)-5 (0.073 g, 0.23 mmol) in methanol (3 ml) to give acid (9Z)-UAB30 (0.065 g, 98% yield) as a yellow solid: mp 182–185° C. (cyclohexane).

(2E,4E,6E,8E)-8-(3',4'-Dihydro-1'(2'H)-naphthalen-1'-ylidene)3,7-dimethyl-2,4,6-octatrienoic acid ((13Z)-UAB30)

This preparation employed a solution of KOH (0.085 g, 1.50 mmol) in water (1 ml) and a warm solution of ester (13Z)-5 (0.040 g, 0.12 mmol) in methanol (4 ml) to give acid (13Z)-UAB30 (0.034 g, 93% yield) as a yellow solid: mp 180–185° C. (cyclohexane).

EXAMPLE 2

Biology of Retinoic Acid Analogues

The chick skin CRABP binding assay measured IC$_{50}$ values for retinoid binding to CRABP-II using a radiolabeled competition assay (8–10). The IC$_{50}$ values for retinoids with RARs and RXRs were measured with a radiolabeled competition assay (8–10). The nuclear receptor transcriptional activity assays were performed using CV-1 cells. Transient transfection of these cells with a DNA plasmid was performed essentially as described in Alam et al (9). The mouse skin antipapilloma assay measured the ED$_{50}$ values for retinoid tumor inhibition on the dorsal skin of mice. The inhibition of mouse skin papilloma by retinoids was performed according to a modification of the procedure developed by Verma and Boutwell (14) as reported previously by Muccio et al. (8).

EXAMPLE 3

Cells

NB4 cells were obtained from Dr. Waxman after he received them from Dr. M. Lanotte. The NB4 cells were maintained in culture in RPMI 1640 (GIBCO, Grand Island, N.Y.) supplemented with 10% (v/v) FBS (fetal bovine serum) (GIBCO) AND 10 mM 4-(2-hydroxyethyl)-1-piperazinethane sulfonic acid (pH 7.3). The cell were grown at 37° C. in a humidified atmosphere of 5% CO$_2$in air. Cell density was estimated on an electronic particle counter (Coulter electronic, Hialeah, Fla.) and cell viability with trypan bleu dye exclusion. NB4 cells were free of mycoplasma as assessed by the mycoplasma Laboratory, PRI/DynCorp, NCI-Frederick Cancer Research and Development center, Frederick, Md., using Hoechst 33258 fluorescent dye and agar cultivation detection methods (Del Giudice et al., 1984 monograph no. 5).

EXAMPLE 4

Inhibition of (all-E)-RA Induced-RARα Transcriptional Activity in CV-1 Cells

The antagonistic effects of UAB30 retinoids on the transcription of RARα were determined in CV-1 cells. The methods are nearly identical to those used to perform transcriptional assays. These studies utilized the CAT reporter gene containing TREpal with a thymidine kinase promoter [(TREpal)$_2$-tk-CAT] as described by Vaezi et al.

(11). Twenty-four hours after transfection, cells were treated with (all-E)-RA (1–1000 nM) alone or together with the indicated UAB retinoid (100 or 1000 nM). After 24 hours, cells were harvested and the transcriptional effects were measured relative CAT activity, after correction with β-gal activity for transfection efficiency. Similar studies were done with a known RARα antagonist, Ro-41-5253. All experiments were performed in triplicate, and the data were averaged. Antagonism was defined as a lowering of the relative CAT activity of transcription induced by (all-E)-RA in the presence of retinoid as compared to positive controls which did not contain retinoid. Both (all-E)-UAB30 and Ro-41-5253 exhibited antagonism at each concentration of (all-E)-RA used to induce transcription, but the effects were most noticeable when (all-E)-RA was 50 nM.

EXAMPLE 5
Retinoid Induction of Differentiation of HL-60 and NB4 Cells

Human leukemia cell line HL-60 and NB4 were used for measuring the ability of retinoids to induce terminal differentiation. Both cell lines are predominantly promyelocytes and are induced by retinoic acid to mature to cells with many characteristics of mature granulocytes. The induction of this differentiation is the basis for assaying one of the biological activities of retinoic acid analogues. For the differentiation assay, HL-60 or NB4 cells were grown in nutrient medium with fetal bovine serum as detailed by Breitman (15).

All-trans-retinoic acid and nitroblue tetrazolium (NBT) were purchased from Sigma Chemical Co. St. Louis, Mo. All-trans- and 9-cis-isomers of UAB8 and UAB30 were synthesized according to the methods described previously (Alam et al. 1995; Muccio et al., 1998). ATRA and UAB retinoids were dissolved in dimethylsulfoxide (DMSO) at a concentration from 0.1 to 10 mM and then diluted 1000-fold for cellular treatment. NB4 cell growth and differentiation was performed according to previously described methods (Breitman, 1990, Methods Enzymol. 190, 118; Taimi & Breitman, 1997, Experimental Cell Research, 230, 69). After 3 days incubation, cell differentiation was assessed by the ability to reduce NBT as the percentage of cells with cell-associated nitroblue diformazan deposits resulting from reducing NBT (Breitman, 1990, Methods Enzymol. 190, 118). The percentage of cells that gained this marker was measured microscopically. The percentage of positive cells was then plotted as a function of the retinoid concentration to determine $ED_{50}$ and $ED_{30}$ values used in the formation of isoboles.

EXAMPLE 6
Transient Transfection Assays for RAR Agonists and Antagonists

Transient transfection assays for ATRA or UAB retinoid-induction of the transcription mediated by either RAR-α or RXR-α were measured using the methods previously reported (Alam et al., 1995, J. Med. Chem. 38, 2302). These assays were performed in CV-1 cells with the RAR or RXR gene and the chloramphenicol acetyltransferase (CAT) reporter gene containing TREpal with a thymidine kinase promoter [(TREpal)$_2$-tk-CAT]. Twenty-four hours after transfection, cells were treated with a single dose of retinoid and the cell extracts were assayed for b-galactosidase and CAT activity. The antagonistic effects of UAB30 retinoids on the transcription of RAR-α were also determined in CV-1 cells. The methods are nearly identical to those used to perform transcriptional assays. These studies utilized the CAT reporter gene [(TREpal)$_2$-tk-CAT]. Twenty-four hours after transfection, cells were treated with ATRA (1 to 1000 nM) alone or together with the indicated UAB retinoid (100 or 1000 nM). After 24 hours, cells were harvested and the transcriptional effects were measured in relative CAT activity, after correction with β-galactosidase activity for transfection efficiency. Similar studies were done with a known RAR-α antagonists, Ro-41-5253. Experiments were performed in triplicate and the data were averaged. Antagonism was defined as a lowering of the relative CAT activity of transcription induced by ATRA in the presence of retinoid as compared to positive controls that did not contain retinoid.

EXAMPLE 7
Transient Transfection Assays for Anti-AP-1 Activity

HeLa cells were transfected with −73 Col-CAT in which the collagenase promoter that contains an AP-1 binding site is linked with the CAT gene together with the indicated retinoid receptor expression vector. Twenty-four hours after transfection, cells were maintained at 0.5% fetal calf serum and treated with the indicated retinoid concentration with or without TPA (100 mg/mL) for 24 hours. Cells were harvested and the CAT activities were determined and corrected with the corresponding β-galactosidase activity for transfection efficiency.

EXAMPLE 8
Inhibition of JMML Spontaneous CFU-GM Colony Formation (all-E)- and (9Z)-RA, UAB8, and UAB30 retinoids were tested for their ability to inhibit spontaneous CFU-GM colony growth in three JMML patient samples as described by Emanuel et al (5, 16). Briefly, after obtaining parental consent and with the approval of the Institutional Review Board, JMML peripheral blood and bone marrow samples were collected from patients and shipped by overnight delivery to the University of Alabama at Birmingham. Mononuclear cells were separated by density gradient centrifugation, washed, and frozen in aliquots. Aliquots of JMML patient samples were later thawed, washed, and set up in 0.3% soft agar clonal assays in McCoy's 5A medium supplemented with nutrients as well as 15% fetal bovine serum. No growth factors or other exogenous stimuli were added to the cultures. UAB retinoids and retinoic acid isomers were dissolved in either 100% ethanol or DMSO. Appropriate dilutions were made, and controls using the respective ethanol or DMSO concentration were set up in parallel. Varying doses of retinoids were added only once, 24 hours after initiation of the soft agar assays, by pipetting the retinoid solution on top of the soft agar and allowing the solution to enter the agar and interact with the cells by diffusion. The cultures were incubated for 14 days at 37° C. in a humidified atmosphere with 5% $CO_2$. CFU-GM colonies (1 colony has >40 cells) were scored, and the resultant amount of inhibition of spontaneous CFU-GM colony growth was compared to the (13Z)-RA.

EXAMPLE 9
Efficacy of UAB-30 on MNU-Induced Mammary Cancers

Female Sprague-Dawley rats were obtained from Harlan Sprague-Dawley, Inc. (virus-free colony number 218). Rats arrived at 28 days of age and placed on Teklad (4%) diet on day of arrival. At 50 days of age, the rats received one IV injection of methylnitrosourea (MNU) (50 mg/kg body weight) via the jugular vein. MNU was purchased from Ash-Stevens, Inc. Beginning at 53 days of age, the rats were administered (9Z)-UAB30 in the diet (200 mg/kg feed). The rats were weighed once a week, palpated for mammary tumors twice a week, and checked daily for signs of toxicity.

Rats' body weights were statistically analyzed 5 weeks, 10 weeks and 15 weeks after the initial administration of (9Z)-UAB30. At 140 days after MNU induction, study was terminated. All mammary tumors were weighted when removed at necropsy, and histologically classified.

EXAMPLE 10

Molecular Modeling

Retinoid structures were generated with Sybyl version 6.2 (Trips Inc., St. Louis, Mo.) on a silicon Graphics Indigo 2 workstation. The structure of (9Z)-2 was built using the recently reported X-ray crystal structure (17). This structure crystallized in the 8-s-trans-conformation. To generate 8-s-cis-conformations, this structure was rotated about the C8–C9 bond followed by energy minimization using Allinger's MM3(94) force fields. The structure of final UAB30 acids were generated from this 8-s-cis- and 8-s-trans-structures of 2. The thermodynamic parameters were calculated according to previously described methods (8).

EXAMPLE 11

Generation of New Compounds

Figure 2:
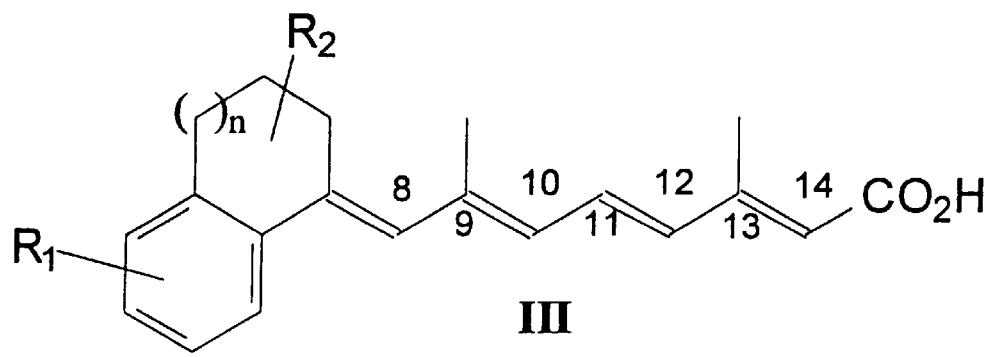
FIG. 2 shows general structures III and IV, which describes UAB30 and analogs, wherein $R_1$ represents one or two substituents on the aryl ring and is selected from the group consisting of H, ethyl, methyl, n-propyl, i-propyl, t-butyl, phenyl, benzyl, chloro, fluoro, methoxy, ethoxy, benzyloxy, cyclic alkyl (from C1–C8), aryl, arylalkyl, alkyloxy, aryloxy, arylalkyloxy, and halogen; $R_2$ is selected from the group consisting of H, ethyl, methyl, n-propyl, i-propyl, 2-methylpropyl, n-butyl, cyclohexyl, 3-cyclohexenyl, benzyl, methoxy, ethoxy, benzyloxy, cyclic alkyl (from C1–C8), aryl, arylalkyl, alkyloxy, aryloxy and arylalkyloxy; and wherein n=0–3.
Figure 2:
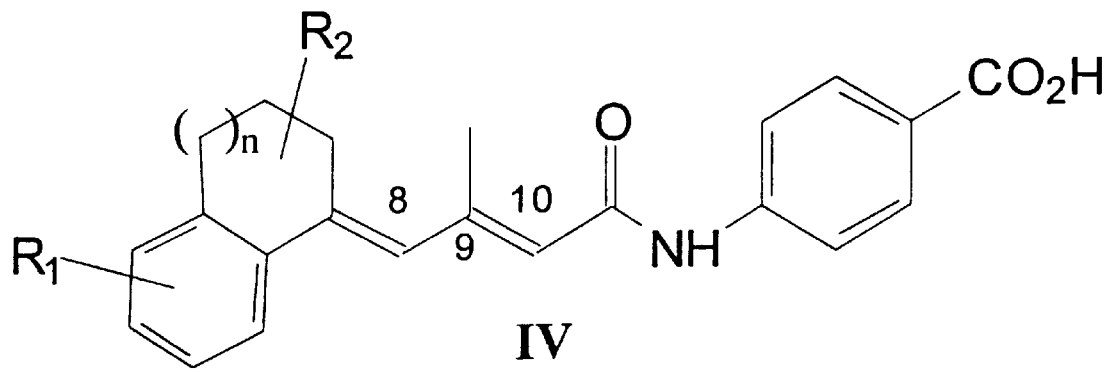

FIG. 3 summarizes the methods employed to prepare UAB30. The approach was similar to that which was previously reported for the synthesis of the alkyl-substituted UAB retinoids (e.g., UAB8) (9, 10), except that α-tetralone was used as the starting enone (1 in FIG. 1). By beginning with appropriate ketones, similar methods were used to prepare all retinoids belonging to general structures I and III (FIGS. 1 and 2). For general structures II and IV (FIGS. 1 and 2), the carboxylic acid intermediate related to compound 2 (FIG. 3) was reacted with methyl 4-aminobenzoate in the presence of hexachloroacetone to give the amide, and the methyl ester subsequently underwent saponification to provide the final products of structures II and IV.

The atom numbering in FIG. 3 is nonsystematic to allow ready comparison with retinoic acid. As noted before (9), a δ-lactone intermediate was not detected under these conditions but was assumed to be an intermediate in the production of (9Z)-2. Unlike earlier reports for related compounds (8–10), the reduction of acid (9Z)-2 to alcohol 3 was accompanied by isomerization to give a 1:1 mixture of all-E- and 9Z-isomers. This mixture was oxidized with $MnO_2$ to give a comparable mixture of aldehydes (4), which were preparatively separated using flash chromatography on silica gel. Each pure isomer of 4 was olefinated as shown to provide a mixture of either (9Z)- and (9Z, 13Z)-5 or (all-E)- and (13Z)-5. Each mixture was preparatively separated by HPLC on silica gel (0.5% $Et_2O$, 0.1% THF in hexane for the former and 1% $Et_2O$, 0.5% THF in hexane for the latter) using methods similar to those described (8–11). Individual isomers of ester 5 were then hydrolyzed to the corresponding acids in KOH, without E/Z-isomerization (12). The isomeric purity for the final acids (>97%) was verified by NMR and reverse-phase HPLC (8–11). Experimental yields and selected data for the intermediates and products in FIG. 1 are summarized in Table 1. The UV/vis spectral data of the purified isomers are given in Table 1, and the complete $^1$H NMR assignments are contained in Table 2.

TABLE 1

Selected Data for New Compounds Produced

| Compound | Isolated percent yield | $R_f$[a] | UV/vis[b] $\lambda_{max}$ | ε | IR[c] C=O | C=C | MS m/z |
|---|---|---|---|---|---|---|---|
| (9z)-2 | 86 | 0.35 | 310 | 14 000 | 1673 | 1618 | ND |
| (9z)- and (all-E)-3 | 67 | 0.21 | 264 | 12 000 | (3334) | 1630 | 214.1 |
| (9z)-4 | 59[d] | 0.48 | 295 | 6 000 | 1662 | 1609 | 212.1 |
| (all-E)-4 | 59[d] | 0.42 | 298 | 8 200 | 1662 | 1605 | 212.1 |
| (9z)-5[e] | 78 | 0.59 | 328 | 29 300 | 1701 | 1602 | 322.2 |
| (all-E)-5 | 92 | 0.57 | 358 | 35 000 | 1708 | 1605 | 322.2 |
| (13Z)-5 | 92 | 0.57 | 358 | 30 000 | 1709 | 1604 | 322.2 |
| (9z)-UAB30[f] | 98 | 0.12 | 328 | 30 200 | 1672 | 1594 | 294.2 |
| (all-E)UAB30 | 93 | 0.09 | 358 | 32 500 | 1672 | 1598 | 294.2 |
| (13Z)-UAB30 | 93 | 0.12 | 359 | 26 000 | 1673 | 1596 | 294.2 |

[a]Values are on silica gel using ether/hexane as eluent: 30% $Et_2O$, 3 and 4; 20% $Et_2O$, 2; 10% $Et_2O$, 5 and UAB30. [b]The wavelength maximum (nm) and extinction coefficients ($M^{-1}cm^{-1}$) were obtained in cyclohexane (5) or methanol (UAB30, 4) at room temp. ND: not determined. [c]The IR stretching frequencies ($cm^{-1}$) were obtained as thin films on NaCl disks. Compound 3 OH stretching frequency is reported in parentheses. [d]Yield for the mixture of E/Z-isomers. [e]Ester 5 was preparatively separated on a Whatman Partisil 10 M20/50 normal phase column with 1.0% $Et_2O$ and 0.5% THF in hexane with a 5-ml/min flow rate (9). Retention times were 138.6 min (13Z), 140.2 min (9Z), and 142.6 min (all-E). Re-injected fractions showed one isomer when monitoring at either 300 or 340 nm. [f]UAB30 isomers were analyzed for isomeric purity by reverse-phase chromatography using a Spherisorb ODS C-18 column with 1% acetic acid in acetonitrile (3:7) with a 1.0-ml/min flow rate. Using 340-nm detection (where each isomer had very similar extinction coefficients), the isomeric ratios were determined from the integrated peak areas. The isomeric ratios were greater than 95% for each isomer.

TABLE 2

$^1$H NMR Chemical Shift Assignments (ppm, TMS) for UAB30 Retinoids at 400 MHz

| Compound | H-1' | H-2' | H-4 | H-3 | H-2 | H-1 | H-8 | H-10 | H-11 | H-12 | H-14 | H-18 | 9Me | 13Me |
|---|---|---|---|---|---|---|---|---|---|---|---|---|---|---|
| α-tetralone | 2.11 | 2.63 | 7.22 | 7.44 | 7.27 | 8.01 | | | | | | 2.94 | | |
| (9Z)-2 | 1.84 | 2.57 | 7.09 | 7.17 | 7.16 | 7.66 | 7.14 | 5.79 | 11.79 | | | 2.80 | 2.13 | |
| (all-E)-3 | 1.82 | 2.70 | 7.09 | 7.16 | 7.15 | 7.58 | 6.39 | 5.62 | 4.29 | | | 2.80 | 1.86 | |
| (9Z)-3 | 1.82 | 2.36 | 7.08 | 7.16 | 7.14 | 7.58 | 6.36 | 5.55 | 4.06 | | | 2.83 | 1.85 | |
| (all-E)-4 | 1.86 | 2.76 | 7.14 | 7.22 | 7.20 | 7.61 | 6.49 | 6.04 | 10.10 | | | 2.83 | 2.35 | |
| (9z)-4 | 1.86 | 2.50 | 7.14 | 7.23 | 7.19 | 7.64 | 6.57 | 6.01 | 9.65 | | | 2.86 | 2.09 | |
| (all-E)-5 | 1.85 | 2.78 | 7.09 | 7.15 | 7.15 | 7.58 | 6.51 | 6.23 | 6.96 | 6.28 | 5.79 | 2.81 | 2.08 | 2.37 |
| (9Z)-5 | 1.83 | 2.41 | 7.12 | 7.19 | 7.19 | 7.64 | 6.47 | 6.11 | 6.64 | 6.23 | 5.75 | 2.85 | 1.98 | 2.23 |
| (13Z)-5 | 1.84 | 2.78 | 7.09 | 7.15 | 7.15 | 7.58 | 6.50 | 6.34 | 6.95 | 7.79 | 5.65 | 2.80 | 2.07 | 2.08 |
| (all-E) | 1.85 | 2.78 | 7.10 | 7.17 | 7.15 | 7.58 | 6.52 | 6.25 | 7.01 | 6.32 | 5.82 | 2.81 | 2.09 | 2.38 |

TABLE 2-continued

¹H NMR Chemical Shift Assignments (ppm, TMS) for UAB30 Retinoids at 400 MHz

| Compound | H-1' | H-2' | H-4 | H-3 | H-2 | H-1 | H-8 | H-10 | H-11 | H-12 | H-14 | H-18 | 9Me | 13Me |
|---|---|---|---|---|---|---|---|---|---|---|---|---|---|---|
| -UAB30 | | | | | | | | | | | | | | |
| (9Z)-UAB30 | 1.84 | 2.41 | 7.12 | 7.20 | 7.20 | 7.59 | 6.48 | 6.12 | 6.69 | 6.25 | 5.77 | 2.85 | 1.99 | 2.23 |
| (13Z)-UAB30 | 1.84 | 2.79 | 7.08 | 7.15 | 7.15 | 7.58 | 6.51 | 6.35 | 7.00 | 7.74 | 5.56 | 2.79 | 2.08 | 2.12 |

EXAMPLE 12

Structure Studies

The X-ray crystal structure of (9Z)-2 was recently reported (17), which crystallized in an 8-s-trans-conformation. To compare the X-ray structure of (9Z)-2 to that generated by molecular mechanics, Allinger's MM3 (94) calculations were performed as described for calculating the structures of UAB1-UAB8 retinoids (8). The calculated structure of this intermediate was very similar to the solid-state structure. The $\psi_{5,6,7,8}$ torsional angles were nearly planar (−160°) in each structure, like other UAB retinoids with alkyl substituents (8). The $\psi_{7,8,9,10}$ torsional angle was −133° for the molecular mechanics structure and −134.3° in the crystal structure. This angle is nonplanar due to steric interactions between the C2' methylene and the C19 methyl group. The molecular mechanics structures of (9Z)- and (all-E)-UAB30 retinoids were also generated. When compared to those of UAB8 isomers (8), the expected low-energy conformers are very similar; the aromatic ring of UAB30 retinoids occupies space that is very similar to that of the alkyl groups (R1=Et; R2=$^i$Pr) of UAB8.

It was previously noted that the 8-s-cis-conformer was as stable as the 8-s-trans-conformer for different UAB retinoids (8). The low-energy structures of the 8-s-cis-conformer of UAB30 isomers were also calculated. The $\psi_{5,6,7,8}$ torsional angles were nearly identical to that of the 8-s-trans-conformer, and the $\psi_{7,8,9,10}$ angle was −70°. Further, the 8-s-cis-conformer was slightly more stable (ΔG≈1 kcal/mol) than the corresponding 8-s-trans-conformer.

Nuclear Overhauser experiments (NOESY) (2D) were performed on (9Z)-2 in CDCl₃. Significant NOEs were observed between H-19 and H-2' (consistent with the 8-s-trans-conformer) and between H-19 and H-8 (consistent with 8-s-cis-conformer). Relative to the very intense cross-peak intensity found between the H-19 methyl protons and H-10 (indicating the 9Z-configuration), the intensities of the negative cross-peaks observed between H-19/H-2' and H-19/H-8 were about one-half this integrated intensity. Similar results were obtained from NOESY experiments on all-E- and 9Z-isomers of UAB30. The NOE results are in support of the MM3 calculations which identified two low-energy conformers about the C8–C9 bond in the polyene chain of these retinoids.

EXAMPLE 13

CRABP Binding Affinity

The IC$_{50}$ values were evaluated in a chick skin CRABP radioligand binding assay with [³H]-(all-E)-RA as the radioligand (18). At 100-fold excess of unlabeled UAB retinoid, (all-E)-UAB30 inhibited the binding of [³H]RA by only 75%; (13Z)-UAB30 (28% inhibition) and (9Z)-UAB30 (5% inhibition) had even less affinity for CRABP. The lower affinity of UAB30 isomers (IC$_{50}$>2000 nM) relative to the all-E-isomers of RA (IC$_{50}$=600 nM) is surprising especially since UAB7 and UAB8 retinoids had binding affinities comparable to that of RA. Apparently, the aromatic ring residues of UAB30 does not interact as well as the bulky alkyl groups of UAB8 in the RA binding site of CRABP, even though these groups are positioned in a similar region of space in solution.

EXAMPLE 14

Nuclear Receptor Binding Affinity and Transcriptional Activity

The all-E-, 9Z-, and 13Z-isomers of UAB30 were evaluated for their ability to inhibit the binding of [³H]-(all-E)-RA to RARs. To survey the inhibition process, nuclear receptors (RARα, RARβ, RARγ, and RXRα) were first exposed to 1000 nM UAB retinoids and 5 nM [³H]-(all-E)-RA. This was compared to a positive control using 1000 nM unlabeled (all-E)-RA and a control using no retinoid. For active retinoids, IC$_{50}$ values were determined by titration with varying concentrations of UAB retinoids. (all-E)-UAB30 was the only UAB30 isomer which efficiently bound to RARs. The IC$_{50}$ values (30–50 nM) for RARs were only about 5-fold greater than that for (all-E)-RA or (all-E)-UAB8 (Table 3) and comparable to that for (9Z)-RA. The IC$_{50}$ values for (9Z)-UAB30 were >1000 nM indicating that it did not bind to RAR receptors (Table 3), which is consistent with data on (9Z)-UAB8, The low affinity for RARs is not shared by (9Z)-RA, which binds nearly as well as (all-E)-RA to these receptors. Also, (13Z)-UAB30 was an ineffective binder to the RAR subtypes, which is different from the binding properties of (13Z)-UAB8 to these nuclear receptors (9).

TABLE 3

IC$_{50}$ and EC$_{50}$ Values[a] (nM) for UAB8 and UAB30 Retinoids in Nuclear Receptor Binding and Transcriptional Activation Assay

| | IC$_{50}$(nM) | | | | EC$_{50}$(nM) | | | | |
|---|---|---|---|---|---|---|---|---|---|
| Retinoid Isomer | RARα | RARβ | RARγ | RXRα | RARα | RARβ | RARγ | RXRα | RARα/RXRα |
| (all-E)-RA | 6 | 5 | 4 | >2000 | 22 | 2 | 6 | >2000 | 32 |
| (9Z)-RA[b] | 31 | 8 | 60 | 82 | 18 | 27 | 10 | 27 | 17 |
| (all-E)-UAB8 | 14 | 6 | 10 | >2000 | 33 | 20 | 2 | >2000 | 68 |

TABLE 3-continued $IC_{50}$ and $EC_{50}$ Values[a] (nM) for UAB8 and UAB30 Retinoids in Nuclear
Receptor Binding and Transcriptional Activation Assay

| Retinoid Isomer | $IC_{50}$(nM) | | | | $EC_{50}$(nM) | | | | |
|---|---|---|---|---|---|---|---|---|---|
| | RARα | RARβ | RARγ | RXRα | RARα | RARβ | RARγ | RXRα | RARα/RXRα |
| (13Z)-UAB8[b] | 900 | 371 | 708 | >1000 | 51 | 150 | 42 | >2000 | 450 |
| (9Z)-UAB8 | >1000 | >1000 | >1000 | 868 | >1000 | >2000 | 190 | 220 | >2000 |
| (all-E)-UAB30 | 35 | 49 | 55 | >2000 | >2000 | 110 | 370 | >2000 | >1000 |
| (13Z)-UAB30 | >1000 | >1000 | >1000 | >2000 | >2000 | >2000 | >2000 | >2000 | >2000 |
| (9Z)-UAB30 | >2000 | >2000 | >2000 | 284 | >2000 | >2000 | >2000 | 118 | >1000 |

[a]The $IC_{50}$ and $EC_{50}$ values were calculated by a Probit analysis of a dose-response curve using concentrations between 1 and 1000 nM. The standard error in the reported $IC_{50}$ values was ±2.0 nM or less. The standard error in the reported $EC_{50}$ values was ±2.5 nM or less, except for the $EC_{50}$ value reported for the activation of RARγ by (9Z)-RA, which was ±4 nM. [b]$IC_{50}$ values were taken from Alam et al (9).

UAB30 isomers were evaluated in assays which measures their functional activity within cells to induce RARα-, RARβ-, and RARγ-mediated transcriptional activity. CV-1 cells were transiently transfected with DNA plasmid from the appropriate RAR subtype and (TREpal)$_2$-tk-CAT (9, 19). Using a dose-response curve, the $ED_{50}$ values for retinoid-induced transcription of UAB30 isomers were measured and then compared to those found for (all-E)- and (9Z)-RA and for (all-E)- and (9Z)-UAB8 (Table 3). (All-E)-UAB30 induced RARβ-mediated receptor -activated transcription; however, 5-fold higher concentrations were needed to achieve similar activation to those observed for (9Z)-RA or (all-E)-UAB8. (all-E)-UAB30 displayed moderate activity in inducing RARγ-mediated transcription and had no activity for inducing RARα transcription. As such this UAB30 isomer displays RARβ and RARγ subtype selectivity and RARα antagonist properties, which is in sharp contrast to (all-E)-UAB8- a very efficient pan-RAR agonist. (13Z)-UAB30 displayed much different nuclear receptors transcriptional properties than its UAB8 analogue; it had no activity in inducing RAR-mediated gene expression, whereas (13Z)-UAB8 was an efficient activator of gene transcription mediated by RARs. (9Z)-UAB30 was even a poorer activator of receptor genes mediated by RARs; it was much less active in these assays than (9Z)-UAB8.

The binding affinity of the UAB30 isomers to RXRα was examined next. Only (9Z)-UAB30 inhibited the binding of 20 nM [³H]-(9Z)-RA to RXRα (Table 3). At 100-fold excess of unlabeled UAB retinoid, (9Z)-UAB30 inhibited 70% of the activity relative to (9Z)-RA. The $IC_{50}$ value for this isomer was better than that for (9Z)-UAB8 and only 4-fold higher than that of (9Z)-RA. The other isomers were much less effective ($IC_{50}$>2000 nM). When the effect on RXRα homodimer-mediated transcriptional activity by (9Z)-UAB30 was about 4-fold less efficient than that by (9Z)-RA but 2-fold better than that by (9Z)-UAB8. Of the (9Z)-UAB isomers, UAB30 is the most potent and selective ligand for activating RXRs.

Since (all-E)-UAB30 bound well to RARα ($IC_{50}$=35 nM) but did not activate this receptor well ($EC_{50}$>1000 nM), its potential to act as an RARα antagonist was evaluated next. Fixed (all-E)-RA concentrations ranging between 1 and 1000 nM were evaluated in the transcriptional assay mediated by RARα homodimers using two concentrations of (all-E)-UAB30 (10 or 100 nM). These were compared to a negative control of (all-E)-RA alone and a positive control using Ro-41-5253, a known RARα antagonist, at 10 and 100 nM. For 50 and 100 nM (all-E)-RA concentrations, the relative CAT activity of the cells treated with 100 nM (all-E)-UAB30 decreased relative to those containing only (all-E)-RA. This decrease in CAT activity is consistent with retinoic acid antagonism by (all-E)-UAB30, but the magnitude of these effects was 2-fold less than that demonstrated by Ro-41-5253.

EXAMPLE 15

Chemoprevention of Mouse Skin Papilloma

The UAB30 retinoids were evaluated next for their activity in preventing the chemical induction of papillomas on mouse skin (14). Both (all-E)-RA and (all-E)-UAB8 were very effective in this chemopreventive assay. At a 45.9-nmol dose, they completely prevented tumor formation (95% for retinoic acid; 99% for UAB8). The $ED_{50}$ values for these retinoids were 3.0 (RA) and 2.5 (UAB8) nmol (8). (all-E)-UAB30 was less effective than this retinoic acid or UAB8 isomer in the skin antipapilloma assay; it only reduced 59% of the papillomas at 45.9 nmol. Using dose-response curves, an $ED_{50}$ could not be accurately determined for this retinoid, consistent with the efforts to quantify the activity of other marginally active UAB retinoids (8). Previously, the high activity of (all-E)-UAB8 (containing large alkyl groups at R1 and R2) was correlated (in structure-activity relationships) to its efficient binding and/or activation of RARs. Using these trends, the reduced activity of (all-E)-UAB30 may be due to its poor ability to activate RARγ and/or lack of ability to activate RARα (Table 3), especially in comparison to (all-E)-UAB8 which has excellent RARγ activity. The (9Z)-UAB8 isomer was also less effective than (9Z)-RA in this assay; it prevented only 54% of tumor formation at 45.9 nmol, a dose at which (9Z)-RA was highly active (95%) (8). This low activity, however, is comparable to that of (9Z)-UAB8 in this assay (8). Since both (9Z)-UAB8 and (9Z)-UAB30 are RXR-selective retinoids, they are not effective activators of RAR-mediated pathways, particularly those mediated by RARβ and RARγ nuclear receptors. Chandraratna et al. (20) showed that RARβ- and RARγ-selective retinoids are excellent inhibitors of TPA-induced ornithine decarboxylase (ODC) activity in skin, an assay which correlates well with the skin antipapilloma assay (14). They suggested that these RARβ- and RARγ-selective retinoids are potent inhibitors of ODC activity in vivo by antagonizing AP-1-mediated ene expression through RARα binding. If this is the case, then (all-E)-UAB30 (a weak RARα antagonist) would not be efficient AP-1 antagonist, but (all-E)-UAB8 should have activity to repress AP-1 gene transcription in addition to its demonstrated potent transcription activity of RAR homodimers (Table 3).

EXAMPLE 16
Transactivation and Transrepression of Nuclear Receptors

Figure 5:
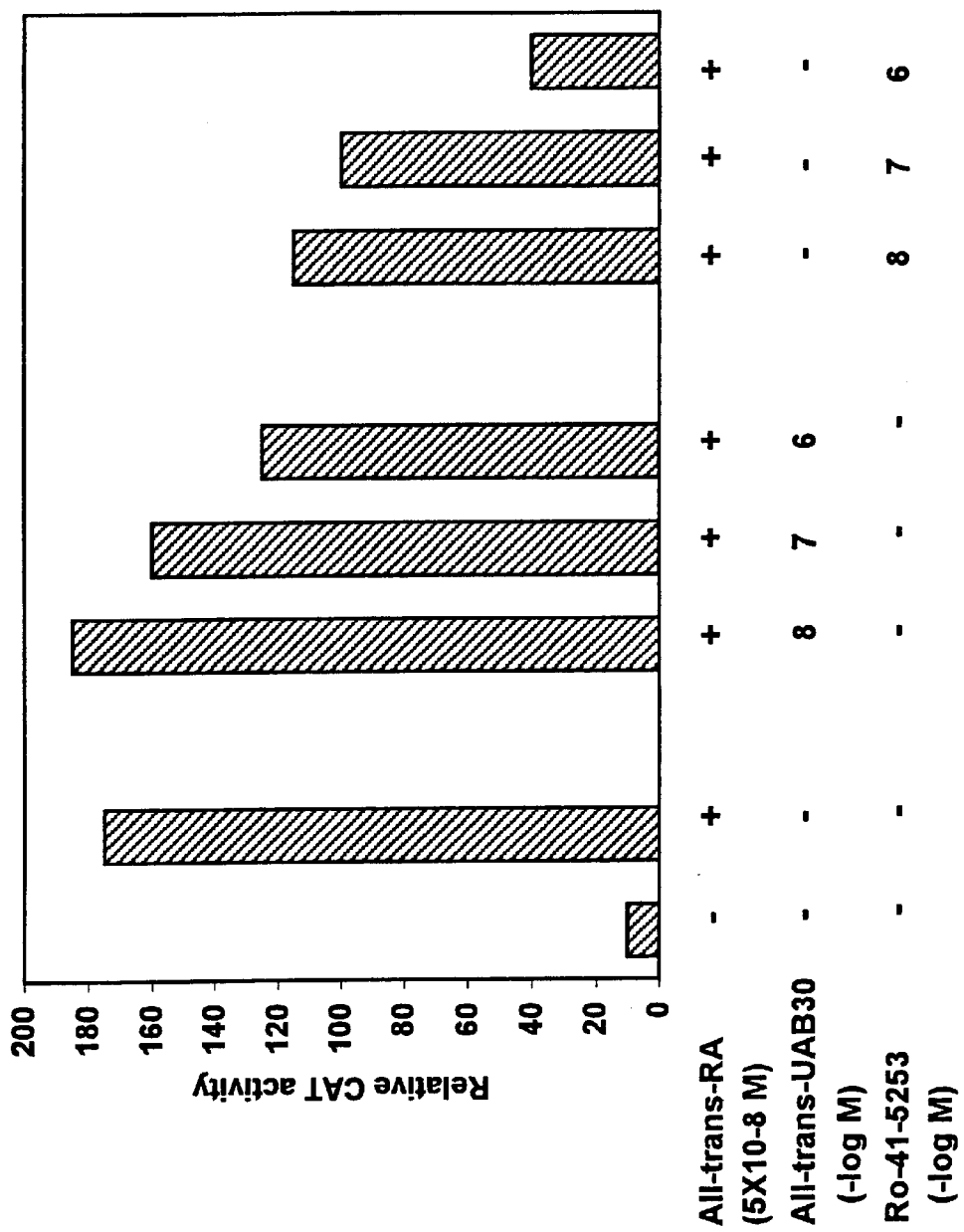
FIG. 5 shows inhibition of all-trans-retinoic acid induced RAR-α transcriptional activity in CV-1 cells by RAR-α antagonists, all-trans-UAB30 and Ro-41-5253. The all-trans-retinoic acid dose was 50 nM, and the doses of all-trans-UAB30 and Ro-41-5253 were varied between $10^{-8}$ to $10^{-6}$ M.

Previously UAB8 and UAB30 retinoids were evaluated in RAR and RXR nuclear receptor binding and transcriptional assays (Muccio et al., 1998). It was found that all-trans-UAB8 is an excellent pan-RAR agonists with similar properties to ATRA. 9-cis-UAB30 was essentially an RXR-selective agonist, with little activity for inducing RAR transcription. 9-cis-UAB8 was similar to 9-cis-UAB30, except it weakly activated RAR-α and RAR-γ. All-trans-UAB30 bound well to each RAR receptor (IC50 values 30–55 nM), but only activated transcription mediated by RAR-β and RAR-γ. To understand if all-trans-UAB30 can act as a RAR-α antagonist, the effects of this retinoid were studied on the RAR-α mediated transcription induced by ATRA. As shown in FIG. 5, increasing doses of all-trans-UAB30 (10 to 1000 nM) depressed RAR-α mediated transcription induced by ATRA at a fixed dose. Ro-41-5253, a known RAR-α antagonist (Apfel et al., 1992, PNAS, 89, 7129) produces a similar trend to that observed by all-trans-UAB30, but it is two-fold more active.

Figure 6:
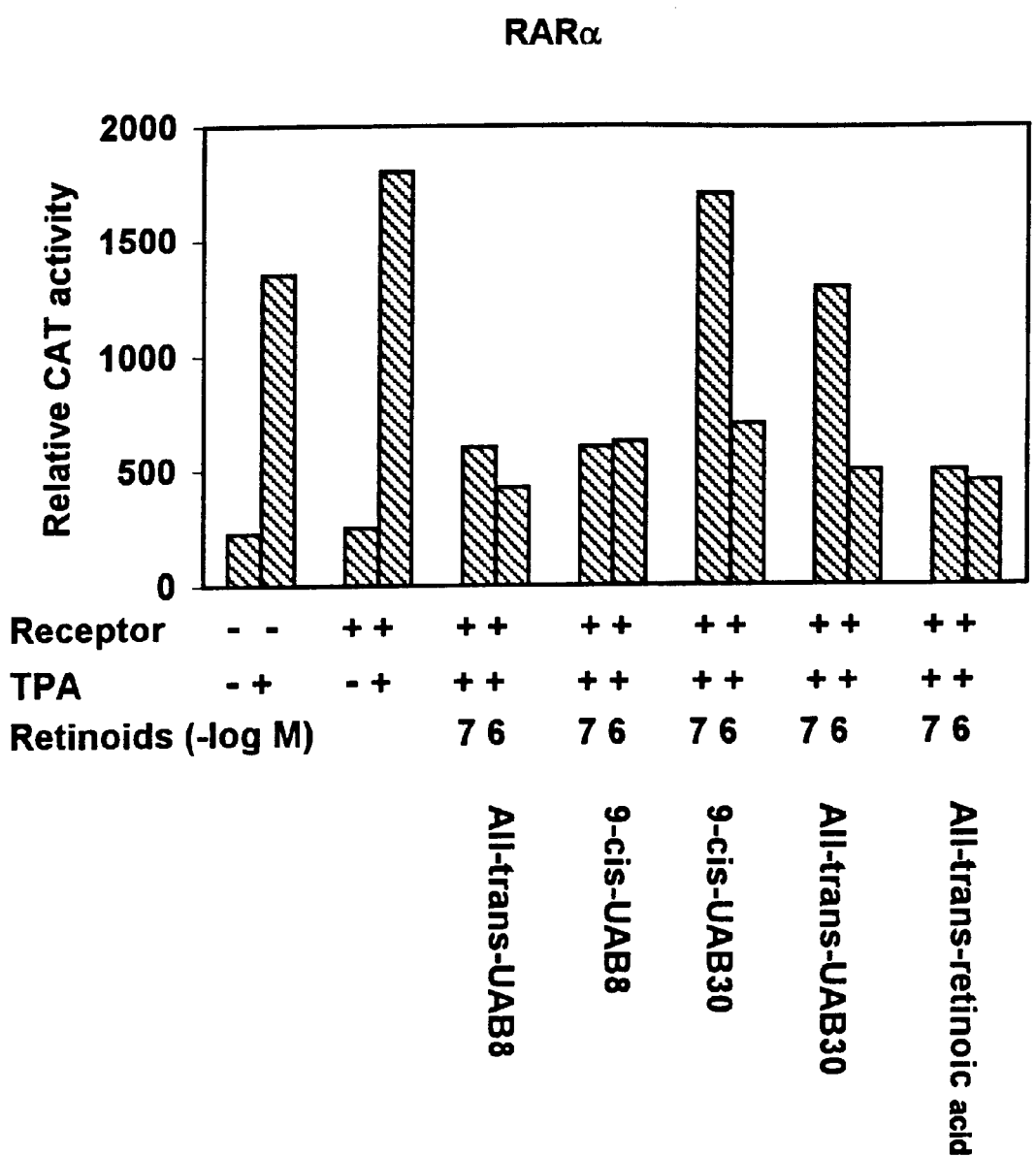
FIG. 6 shows inhibition of TPA-induced RAR-α transcriptional activity in HeLa cells by all-trans-retinoic acid (ATRA), and UAB8 and UAB30 isomers at two doses ($10^{-7}$ and $10^{-6}$ M).

ATRA represses AP-1 (c-Jun/c-Fos) gene transcription in a dose dependent manner. To study the UAB retinoids, the collagenase promoter that contains an AP-1 binding site linked with the CAT gene was used. Together with the RAR-α retinoid receptor expression vector, the repression of TPA-induced gene expression was measured for the different UAB retinoids relative to ATRA. As shown in FIG. 6, all-trans-isomers of UAB8 and UAB30 were both as effective as ATRA in reducing TPA-induced gene expression. The 9-cis-isomers of UAB8 and UAB30 retinoids were only effective at high doses. Thus, all-trans-UAB8 shares the properties of ATRA; it is an excellent pan-RAR agonist and is very active in AP-1 transrepression. Interestingly, all-trans-UAB30 only represses AP-1 transcription like other retinoids discovered (Fanjul et al., 1994, Nature, 372, 107; Nagpal et al., 1995, J. Biol. Chem. 270, 923).

EXAMPLE 17
Retinoid-Induced Differentiation of HL-60 and NB4 Cells

Figure 7:
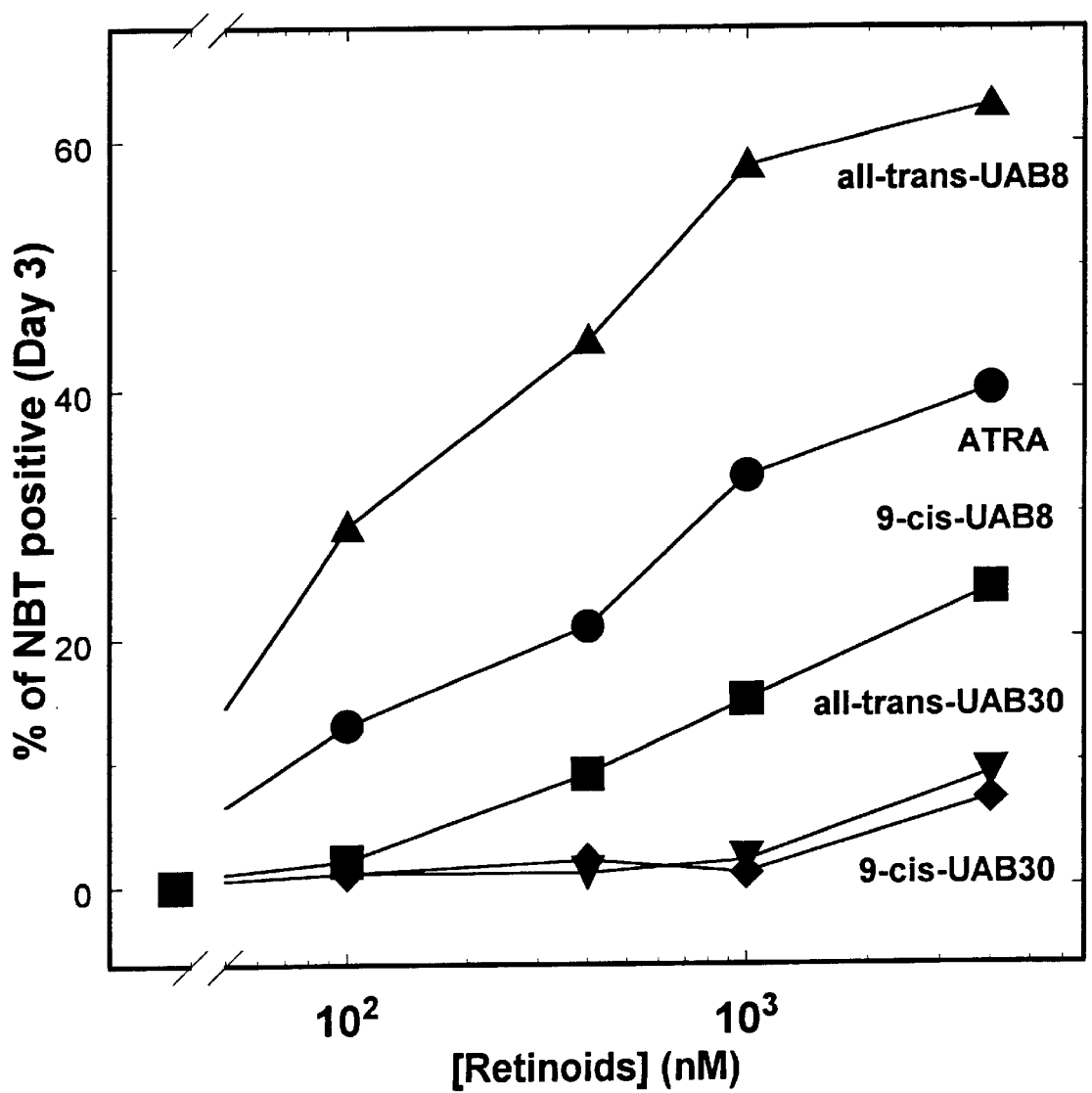
FIG. 7 shows NB4 cells differentiation by ATRA (solid circles), all-trans-UAB8 (solid triangles), 9-cis-UAB8 (solid squares), all-trans-UAB30 (upside-down solid triangles), and 9-cis-UAB30 (solid diamonds). Cells were growth for 3 days in medium supplemented with 10% FBS and the indicated concentration of each retinoids. Differentiation was assessed as the percentage of NBT-positive cell.

To explore the potential of UAB retinoids for treatment of APL, UAB8 and UAB30 isomers were evaluated in in vitro assays which measure their ability to induce differentiation of two APL leukemia cell lines, HL-60 and NB4 cells. Even though HL-60 cells were isolated from APL patients, only the NB4 cell line contains the t (15;17) translocation involving the RARα to form the RARα/PML fusion protein. Because this characteristic mutation is stably carried in NB4 cells, it is a better model for judging retinoid efficacy for this disease. A comparison of the efficiency that ATRA and other UAB retinoids induce differentiation of NB4 cells after 3 days is displayed in FIG. 7. All-trans-UAB8 is about 10-fold more active than ATRA for a range of doses ($ED_{30}$ 110 versus 810 nM). 9-cis-Retinoic acid activity is comparable to that of ATRA (data not shown); however, the activity of 9-cis-UAB30, a highly RXR-selective ligand, has little activity even at doses greater than 1 mM ($ED_{30}$>10 mM). In contrast to all-trans-UAB8, all-trans-UAB30 is not active up to 40 mM consistent with its antagonism of the RAR-α nuclear receptor. The activity of 9-cis-UAB8 is only 50% as active as ATRA ($ED_{30}$>3 mM). This activity may be due to its ability to activate RAR-α mediated transcription at high doses (Muccio et al., 1998).

EXAMPLE 18
NB4 Cell Differentiation using Retinoids in Combination

Figure 8A:
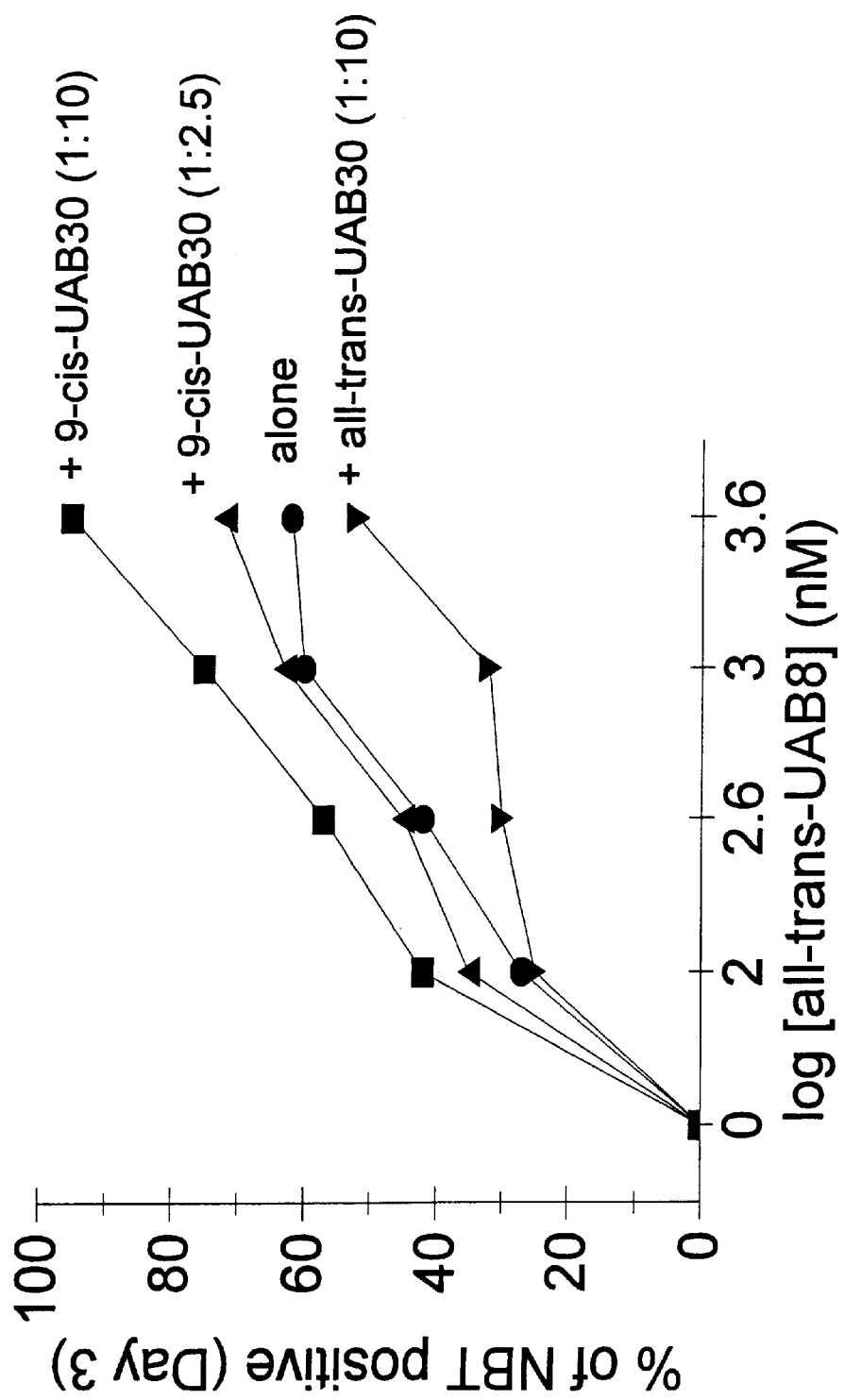
FIG. 8A shows the capacity of all-trans-retinoic acid (ATRA) to differentiate NB4 cells (solid circles) alone or in combination with 9-cis-UAB8 (1:2.5) (solid triangles), 9-cis-UAB30 (1:10) (solid squares), or all-trans-UAB30 (1:10) (solid diamonds).
Figure 8B:
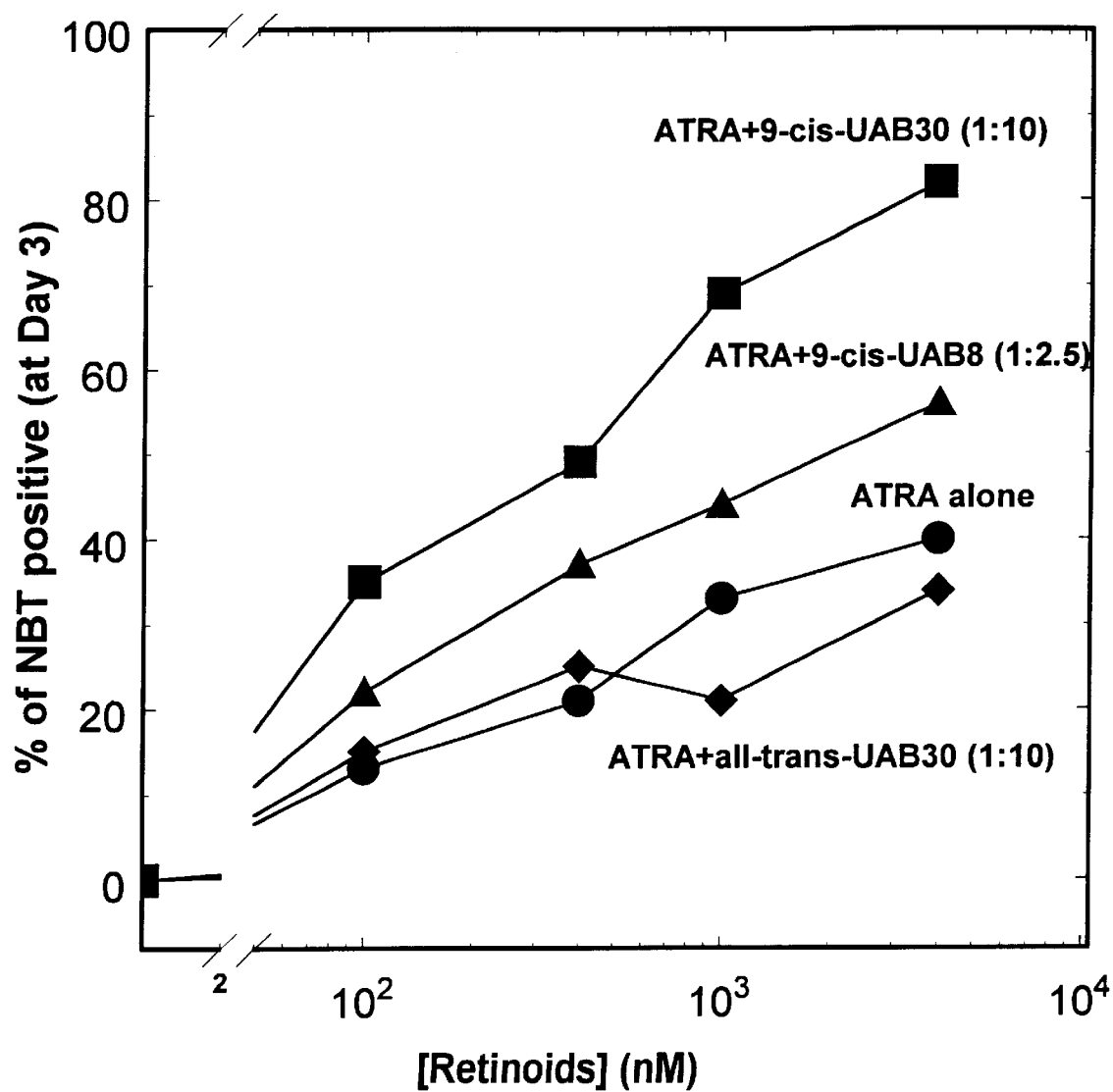
FIG. 8B shows the capacity of all-trans-UAB8 to differentiate NB4 cells (solid circles) alone or in combination with 9-cis-UAB8 (1:2.5) (solid triangles), 9-cis-UAB30 (1:10) (solid squares), or all-trans-UAB30 (1:10) (solid diamonds).

The potential synergistic effects were next explored of using RAR- and RXR-agonists in combination on NB4 cell differentiation. As displayed in FIG. 8A, NB4 cells were treated with varying doses of ATRA alone and in combination with UAB8 and UAB30 isomers. The doses of the UAB8 and UAB30 retinoids were chosen to allow for nearly equal activity of each retinoid relative to ATRA (Berenbaum, 1989, Pharmacol. Rev. 41:93). When NB4 cells were treated with ATRA and 9-cis-UAB30, a 10-fold decrease occurred in the $ED_{30}$ value (day 3) for the differentiation of NB4 cells. Since 9-cis-UAB30 alone had no effect on NB4 cell differentiation (FIG. 7), this is a clear sign of synergy between these two retinoids. 9-cis-UAB30 potentiated the effect of ATRA and shifted the $ED_{30}$ from 810 to 50 nM (ATRA:9-cis-UAB30=1:10). Similar effects were also observed for NB4 cell differentiation using all-trans-UAB8 in combination with 9-cis-UAB8 (FIG. 8B); the shift in $ED_{30}$ was from 110 to 25 nM. The synergistic effects are not as apparent using 9-cis-UAB8; however, when isoboles are made synergy is also observed (Breitman). Synergy between RAR- and RXR-selective agonists has been observed in NB4 cells (Chen et al., 1996, Nature, 382:819) using other retinoid analogs. The effects observed here are comparable to those produced using the RXR-selective ligand BMS649 (SR11237) and other RAR-selective agonists.

Combination effects were also evaluated between ATRA and all-trans-UAB30 to evaluate the effects of an RAR-a antagonists on the differentiation of NB4 cells. The effects of combination were most apparent at high ATRA doses (FIG. 8A) were the $ED_{30}$ increased from 810 to 2800 nM. In similar studies with all-trans-UAB8 (FIG. 8B), all-trans-UAB30 increased the $ED_{50}$ values by about 5-fold (from 660 to 3000 nM). Since all-trans-UAB30 is capable of repressing AP-1 transcription but is inactive in NB4 cell differentiation, it is unlikely that this mode of action plays an important role for NB4 cell differentiation. Instead, the antagonism of both ATRA-induced or all-trans-UAB8-induced NB4 cell differentiation by all-trans-UAB30 is most consistent with a mechanism of action involving RAR-α.

Figure 9:
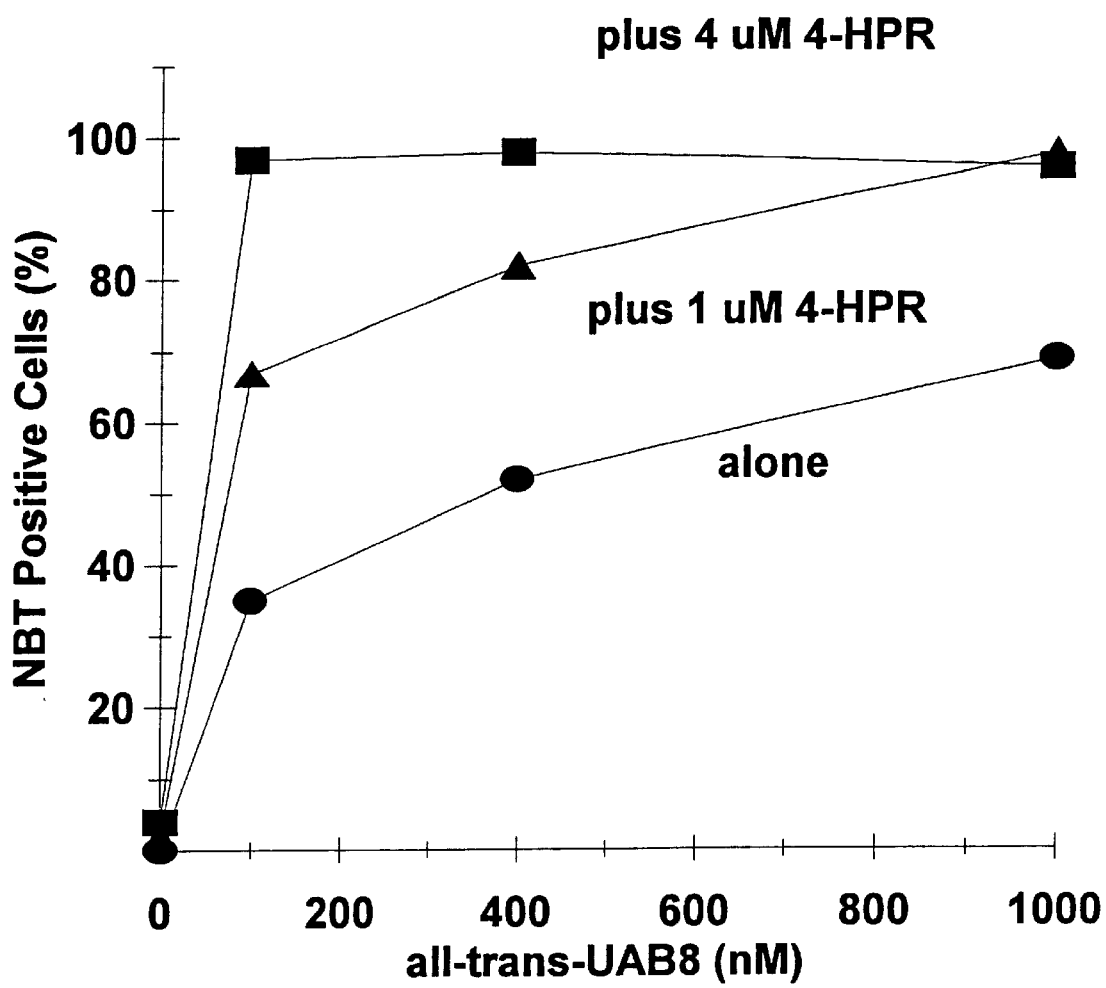
FIG. 9 shows the capacity of all-trans-UAB8 to differentiate NB4 cells (solid circles) alone or in combination with 4-hydroxyphenylretinamide at 1 μM (solid triangles ) and 4 μM (solid squares).

Previously Breitman and coworkers have shown that 4-hydroxyphenylretinamide (4-HPR) alone does not induce NB4 cells to differentiate, but when it is used in combination with all-trans-retinoic acid, differentiation of NB4 cells was enhanced. The combination use of all-trans-UAB8 with 4-HPR was studied here to determine if a similar effect could be induced. NB4 cell ifferentiation was significantly enhanced when cells were exposed to 1 and 4 uM 4-HPR with varying concentrations of all-trans-UAB8 (FIG. 9). The ED50 values of all-trans-UAB8 were shifted 100-fold lower (50 nM) with addition of 4-HPR.

EXAMPLE 19
Retinoid Metabolism in NB4 Cells

NB4 cells were isolated from an APL patient that developed clinical resistance to ATRA treatment (Lanotte et al, 1991, Blood, 77:1080). These cells metabolize ATRA rapidly involving an inducible cytochrome P450 hydroxylase (White et al., 1996, J BC, 271:29922). This metabolism rapidly reduces the effectiveness of ATRA, and potential inhibitors of this enzyme improve the effectiveness of this hormone in NB4 cell differentiation.

EXAMPLE 20
Inhibition of JMML CFU-GM Colony Formation

In 1991, Emanuel et al. (21) demonstrated that the spontaneous CFU-GM colony formation observed in JMML is related to the selective hypersensitivity of JMML hematopoietic progenitor cells to granulocyte-macrophage colony-stimulating factor (GM-CSF). Since this initial report, others

(22) have confirmed these observations of GM-CSF hypersensitivity as a pathogenetic mechanism in JMML. Additionally in 1991, Castleberry, Emanuel, and co-workers also presented preliminary evidence of the ability of (13Z)-RA to inhibit an in vitro JMML spontaneous CFU-GM growth as well as evidence for its possible clinical effectiveness in JMML (21). This pilot clinical trial suggested that the effects of (13Z)-RA in the in vitro screen agree with its efficacy in treating patients with JMML in the clinic (5). In this study, (all-E)- and (9Z)-RA were first evaluated in this in vitro assay and it was shown that these RA isomers also have excellent potential to inhibit spontaneous CFU-GM colony growth in cells isolated from three patients with JMML (Table 4).

The effects of UAB8 and UAB30 isomers on the inhibition of proliferation of human JMML cells were studied next. UAB8 isomers were evaluated in this assay using cells from two patients (Table 4). (all-E)-UAB8 was as effective as (all-E)-RA in controlling the spontaneous growth of these CFU-GM colonies. However, (9Z)- and (13Z)-UAB8 were less effective than the corresponding RA isomers in controlling growth. In particular for patient J84 cells, there is a 2-fold decrease in activity of these retinoids. For UAB30 isomers, the most potent isomer is (13Z)-UAB30 which has activity in two patients only slightly less than that of RA. In contrast to UAB8 isomers, the all-E isomers of this retinoid is less active than RA and (all-E)-UAB8. Also, (9Z)-UAB30 exhibits lower activity in this assay, similar to that of (9Z)-UAB8.

gene expression in JMML, Emanuel (22) have noted an apparent constitutive upregulation of both c-jun and c-fos, but not c-myc. Pfahl (24) demonstrated in epithelial cells (25), that the mechanism by which RA represses gene transcription mediated by AP-1 is cell line-specific and may be mediated by either RARs and RXRs.

The precise mechanism for the high activity of (13Z)-RA in inhibiting the proliferation of these myeloid progenitor cells in JMML remains an area of investigation. Assuming a receptor-based mechanism, (13Z)-RA isomer may isomerize to either (all-E)- or (9Z)-RA and interact with RAR/RXR receptors. The present invention demonstrates that these latter two isomers are as active as (13Z)-RA in preventing proliferation in JMML cells, supporting this assumption. To probe RAR/RXR-mediated pathways, the ability of receptor-selective retinoids to prevent proliferation of JMML cells were investigated. The high activity of (all-E)-UAB8 in this in vitro JMML assay and reduced activity of either (9Z)-UAB8 or (9Z)-UAB30, two RXR-selective retinoids, are consistent with a RAR-mediated pathway of transrepression. (all-E)-UAB30 is less active than the other natural RA isomers and (all-E)-UAB8. Since it binds well to each RAR subtype, but does not activate transcription for RARα antagonist), this lower activity in the in vitro JMML assay relative to (all-E)-UAB8 may be due to its RARα antagonism, or in other words, lack of AP-1 antagonism. Ligand binding is a necessary but not sufficient condition for AP-1 antagonism. This is not an unusual property of retinoids, since retinoids have been identified that are RARα

TABLE 4

$ED_{50}$ Values[a] (nM) for 4-day Induction of Differentiation of HL-60 and NB4 Cellls and Normalized Percent Inhibition[b] of CFU-GM Colony Growth of JMML Cells from 3 Patients

| Retinoid Isomer | ED50 (nM) | | patient J43 (%) | | patient J83 (%) | | patient J84 (%) | | |
|---|---|---|---|---|---|---|---|---|---|
| | HL-60 | NB4 | $10^{-6}$M | $10^{-7}$M | $10^{-6}$M | $10^{-7}$M | $10^{-6}$M | $10^{-7}$M | $10^{-8}$M |
| (all-E)-RA | 120 | 610 | 100 | 74 | 100 | 88 | 100 | 52 | 33 |
| (13Z)-RA | NT[c] | NT | 109 | 100 | 94 | 86 | 87 | 52 | 5 |
| (9Z)-RA | NT | NT | 100 | 98 | 82 | 72 | 95 | NT | NT |
| (all-E)UAB8 | >10000 | 320 | 98 | 85 | | NT | 103 | 51 | NT |
| (13Z)-UAB8 | >10000 | 280 | 80 | 61 | | NT | 49 | 18 | 0 |
| (9Z)-UAB8 | 3400 | 910 | 79 | 52 | | NT | 59 | 38 | 13 |
| (9Z, 13Z)-UAB8 | >10000 | >10000 | 59 | 32 | | NT | 44 | 23 | 20 |
| (all-E)-UAB30 | >10000 | >10000 | NT | | 72 | 68 | 57 | 48 | 28 |
| (13Z)-UAB30 | >10000 | >10000 | NT | | 88 | 82 | 80 | 72 | 25 |
| (9Z)-UAB30 | 8000 | 10000 | NT | | 79 | 76 | 39 | 44 | 3 |

[a]ED50 values were determined from a dose-response curve using four concentrations of retinoids ranging from $10^{-2}$ to 10 μM. [b]Normalized percent inhibition was calculated by (% inhibition of retinoid)/(% inhibition of (all-E)-RA at $10^{-6}$M). The percent inhibition of (all-E)-RA at $10^{-6}$ M was 85%, 78% and 61% for the J43, J83 and J84 patient cells, respectively. [c]NT means not tested.

There are no consistent chromosomal abnormalities in JMML, and none that appear to involve the retinoid receptors. However one very plausible mechanism (23) to explain the apparent modulating effects of RA on GM-CSF hypersensitivity in JMML is through the RA-induced antagonistic effects of RARα on the transcription factor, AP-1 (c-jun/c-fos). The GM-CSF signal transduction cascade through Ras appears to have as one of its major endpoints an upregulation or activation of the AP-1 response element. This response element is activated by c-jun/c-fos, and when stimulated by extracellular signaling (e.g., GM-CSF), induction of AP-1 leads to cellular proliferation, among other processes. In fact in Northern blot experiments investigating early response antagonists but do not induce RAR-mediated transrepression of AP-1 mediated transcription (26).

EXAMPLE 21
Prevention of Cancer by UAB Retinoids

Figure 10:
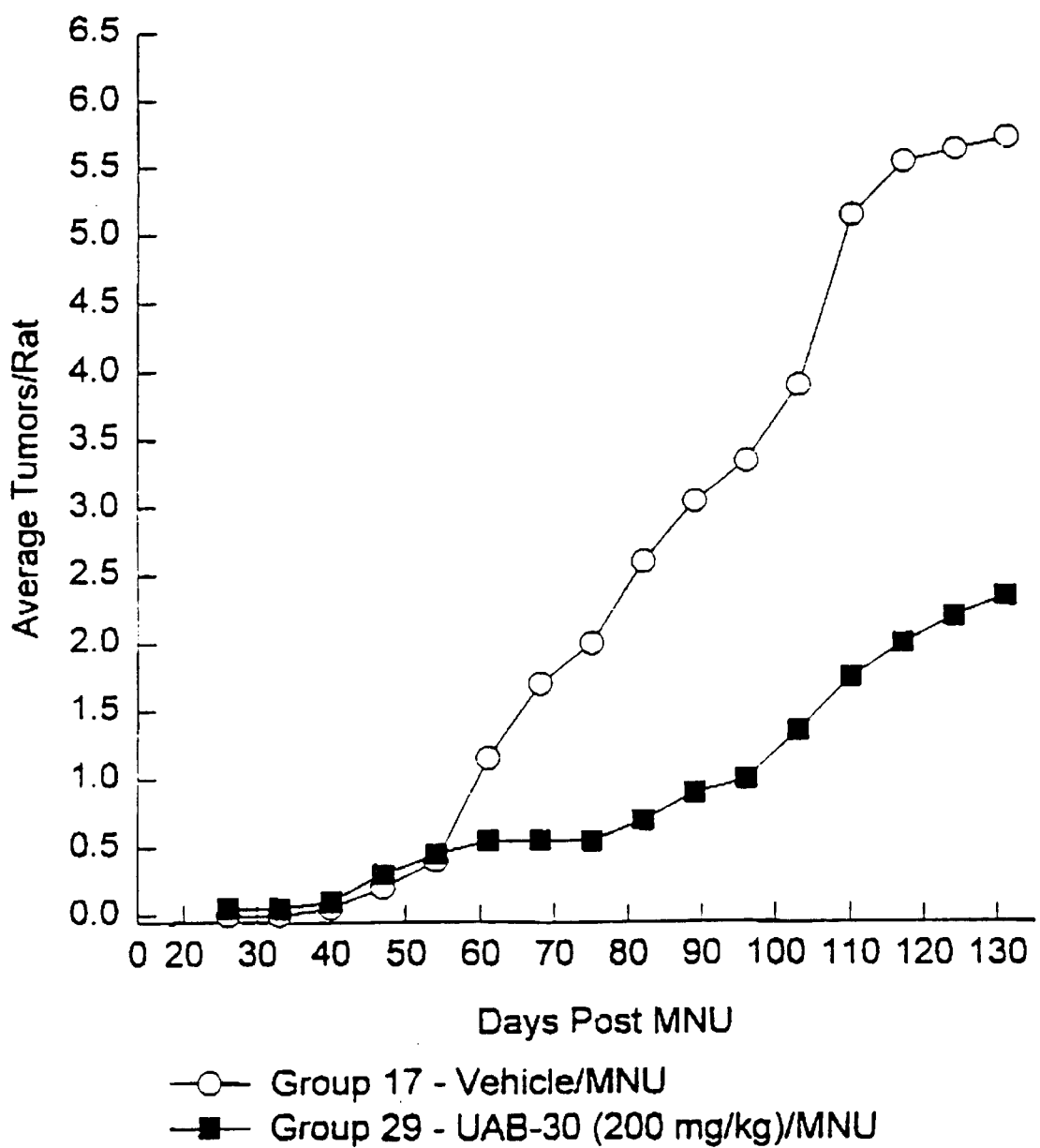
FIG. 10 shows average mammary tumor weight/rat (grams) over a period of time post methylnitrosourea (MNU) induction. Group 17 rats were treated with Vehicle (Teklad diet) (circles), while Group 29 with UAB-30 (200 mg/kg diet) (solid squares).
Figure 11:
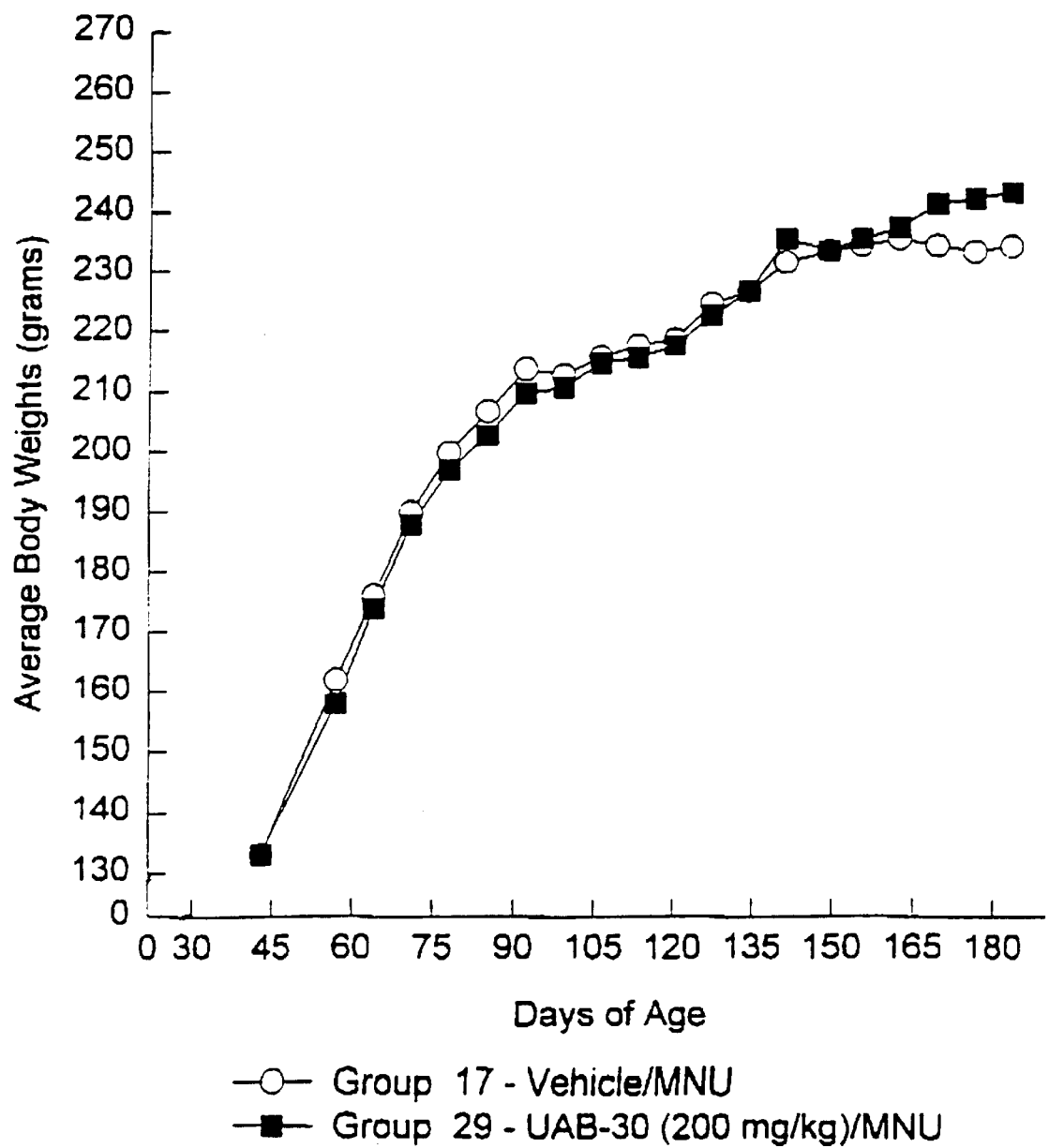
FIG. 11 shows average body weight/rat (grams) over different days of age. Group 17 rats were treated with Vehicle (Teklad diet) (circles), while Group 29 with UAB-30 (200 mg/kg diet) (solid squares).

The efficacy of (9Z)-UAB30 on methylnitrosourea (MNU)-induced mammary cancers was determined. Table 5 and FIG. 10 show the comparison between two groups of rats of average tumor weight/rat over a period of time post MNU induction. Table 6 and FIG. 11 show the comparison between the same two groups of rats of the average body weight/rat measured at different days. The data demonstrate that UAB-30 treatment inhibited the growth of the MNU-induced mammary cancers, while had no obvious effect to the overall body growth.

TABLE 5

| Days post MNU | Group 17 | Group 29 |
|---|---|---|
| 26 | 0 | 0.05 |
| 33 | 0 | 0.05 |
| 40 | 0.05 | 0.10 |
| 47 | 0.20 | 0.30 |
| 54 | 0.40 | 0.45 |
| 61 | 1.15 | 0.55 |
| 68 | 1.70 | 0.55 |
| 75 | 2.00 | 0.55 |
| 82 | 2.60 | 0.70 |
| 89 | 3.05 | 0.90 |
| 96 | 3.35 | 1.00 |
| 103 | 3.90 | 1.35 |
| 110 | 5.15 | 1.75 |
| 117 | 5.55 | 2.00 |
| 124 | 5.65 | 2.20 |
| 131 | 5.75 | 2.35 |

Group 17 - Teklad (4%)/MNU
Group 29 - UAB-30 (200 mg/kg)/MNU

TABLE 6

| Days of Age | Group 17 | Group 29 |
|---|---|---|
| 43 | 133 | 133 |
| 57 | 162 | 158 |
| 64 | 176 | 174 |
| 71 | 190 | 188 |
| 78 | 200 | 197 |
| 85 | 207 | 203 |
| 92 | 214 | 210 |
| 99 | 213 | 211 |
| 106 | 216 | 215 |
| 113 | 218 | 216 |
| 120 | 219 | 218 |
| 127 | 225 | 223 |
| 134 | 227 | 227 |
| 141 | 232 | 236 |
| 149 | 234 | 234 |
| 155 | 235 | 236 |
| 162 | 236 | 238 |
| 169 | 235 | 242 |
| 176 | 234 | 243 |
| 183 | 235 | 244 |

Group 17 - Teklad (4%)/MNU
Group 29 - UAB-30 (200 mg/kg)/MNU

EXAMPLE 22
Examples of Compounds Related to UAB8

The following listed are examples of synthesized compounds that are related to UAB8, with analytical data:

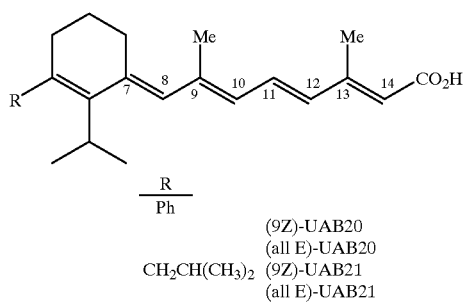

| R | Ph |
|---|---|
|  | (9Z)-UAB20 |
|  | (all E)-UAB20 |
| $CH_2CH(CH_3)_2$ | (9Z)-UAB21 |
|  | (all E)-UAB21 |

(all E)-UAB20 mp 169–171° C. (ether/hexane); $^1$H NMR (300 MHz, $CDCl_3$) δ 7.35–7.31 (m, 2H), 7.23–7.21 (m, 1H), 7.11 (d, 2H), 6.97 (dd, 1H), 6.30 (d, 1H), 6.24 (s, 1H), 6.15 (d, 1H), 5.80 (s, 1H), 2.90–2.77 (m, 1H), 2.59 (t, 2H), 2.38 (s, 3H), 2.33 (t, 2H), 2.03 (s, 3H), 1.78–1.74 (m, 2H), 1.11 (d, 6H).

(9Z)-UAB20 mp 208–210° C. (ether/hexane); $^1$H NMR (300 MHz, $CDCl_3$) δ 7.36–7.32 (m, 2H), 7.27–7.22 (m, 1H), 7.15–7.13 (m, 2H), 6.74 (dd, 1H), 6.24 (d, 1H), 6.17 (s, 1H), 6.07 (d, 1H), 5.78 (s, 1H), 2.93–2.78 (m, 1H), 2.34 (t, 2H), 2.30 (s, 3H), 2.24 (t, 2H), 1.96 (s, 3H), 1.78–1.70 (m, 2H), 1.14 (d, 6H).

(all E)-UAB21 mp 146–148° C. (ether/hexane); H NMR (300 MHz, $CDCl_3$) δ 6.98 (dd, 1H), 6.27 (d, 1H), 6.1 (d, 1H), 6.08 (s, 1H), 5.78 (s, 1H), 3.23–3.08 (m, 1H), 2.48 (t, 2H), 2.36 (s, 3H), 2.11–2.04 (m, 4H), 2.00 (s, 3H), 1.89–1.76 (m, 1H), 1.65–1.56 (m, 2H), 1.21 (d, 6H), 0.90 (d, 6H).

(9Z)-UAB21 mp 159–162° C. (ether/hexane); $^1$H NMR (300 MHz, $CDCl_3$) δ 6.70 (dd, 1H), 6.20 (d, 1H), 6.02 (d, 1H), 5.99 (s, 1H), 5.75 (s, 1H), 3.23–3.11 (m, 1H), 2.25 (s, 3H), 2.12–1.92 (m, 6H), 1.87 (s, 3H), 1.85–1.76 (m, 1H), 1.63–1.55 (m, 2H), 1.24 (d, 6H), 0.91 (d, 6H).

EXAMPLE 23
Examples of Compounds Related to UAB30

The following listed are examples of synthesized compounds that are related to UAB30, with analytical data:

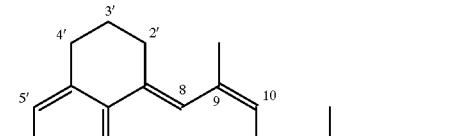

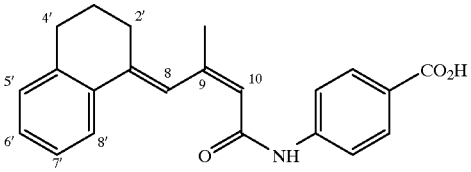

| UAB Number | Substituent(s) | UAB Number |
|---|---|---|
| (9Z)-UAB30 | H | (9Z)-UAB60 |
| (9Z)-UAB31 | 5'-methoxy | (9Z)-UAB61 |
| (9Z)-UAB32 | 6'-methoxy |  |
| (9Z)-UAB33 | 7'-methoxy | (9Z)-UAB62 |
| (all E)-UAB33 | 7'-methoxy |  |
| (9Z)-UAB34 | 4'-methyl |  |
| (9Z)-UAB35 | 5',7'-dimethyl |  |

(9Z)-UAB31

$^1$H NMR: (t) 1H δ7.17 J=7.95, (d) 1H δ6.77 J=7.96, (dd) 1H δ6.67 J=11.10, 4.06, (s) 1H δ6.46, (d) 1H δ6.25 J=15.34, (d) 1H δ6.12 J=11.0, (s) 1H δ5.76, (t) 2H δ2.75 J=6.30, (t) 2H δ2.34 J=5.86, (s) 3H δ2.21, (s) 3H δ1.98, (qui) 2H δ1.84 J=6.10.

(9Z)-UAB32

$^1$H NMR: (d) 1H δ7.60 J=8.79, (m) 3H δ6.79–6.65, (s) 1H δ6.36, (d) 1H δ6.25 J=15.32, (d) 1H δ6.10 J=10.94, (s) 1H δ5.77, (s) 3H δ3.81, (t) 2H δ2.83 J=6.20, (t) 2H δ2.38 J=6.05, (s) 3H δ2.23, (s) 3H δ1.98, (qui) 2H δ1.82 J=6.1.

(9Z)-UAB33

¹H NMR: (d) 1H δ7.16 J=2.54, (d) δ7.06 J=8.40, (dd) 1H δ6.80 J=2.56 J=5.81, (dd) 1H δ6.68 J=4.24 J=11.02, (s) 1H δ6.45, (d) 1H δ6.26 J=15.32, (d) 1H δ6.13 J=10.85, (t) 2H δ2.79 J=6.20, (t) 2H δ2.38 J=5.20, (s) 3H δ1.98, (qui) 2H δ1.81 J=6.17; ¹³C NMR (CDCl₃): δ172.10, 158.27, 155.90, 141.60, 138.71, 136.92, 134.29, 134.18, 130.69, 130.57, 127.82, 122.98, 117.81, 114.59, 109.34, 55.80, 29.81, 28.92, 25.12, 24.45, 14.46; UV-VIS: $1_{max}$=332 nm, e=19838.

(all E)-UAB33

¹H NMR (dd) 1H δ7.58 J=3.73, 1.84, (m) 4H δ7.20–6.97, (s) 1H δ6.51, (d) 1H δ6.33 J=15.05, (d) 1H δ6.25 J=11.4, (s) 1H δ5.82, (m) 4H δ2.83–2.76, (s) 3H δ2.39, (s) 3H δ2.09, (qui) 2H δ1.85 J=6.27.

(9Z)-UAB34

¹H NMR: (d) 1H δ7.63 J=7.29, (m) 4H δ7.26–7.17, (m) 1H δ6.74–6.66, (s) 1H δ6.46, (d) 1H δ6.26 J=15.35, (d) 1H δ6.13 J=15.35, (s) 1H δ5.77, (m) 2H δ3.00–2.92, (m) 1H δ2.54–2.30, (s) 3H δ2.23, (s) 3H δ1.99, (m) 2H δ1.64–1.54, (d) 3H δ1.30 J=6.98.

(9Z)-UAB35

¹H NMR: (s) 1H δ7.33, (s) 1H δ6.95, (dd) 1H δ6.68 J=4.23 J=11.04, (s) 1H δ6.41, (d) 1H δ6.25 J=15.33, (d) 1H δ6.12 J=10.98, (s)1H δ5.76, (t) 2H δ2.68 J=6.36, (s) 3H δ2.32, (m) δ2.36–2.27, (s) 3H δ2.22, (s) 3H δ1.97, (qui) 2H δ1.85, J=6.24; ¹³C NMR(CDCl₃):

(9Z)-UAB40

¹H NMR (DMSO): (s) 1H δ12.03, (m) 4H δ7.23–7.05, (d) 1H δ6.37 J=15.40, (d) 1H δ6.18 J=11.51, (s) 1H δ6.07, (s) 1H δ5.78, (s) 2H δ2.74, (s) 2H δ2.30, (s) 3H δ2.20, (s) 3H δ2.00, (s) 4H δ1.66.

(9Z)-UAB60

¹H NMR: (s) 1H δ8.18, (d) 2H δ7.90 J=8.71, (d) 1H δ7.69 J=7.66, (d) 2H δ7.43 J=8.73, (m) 3H δ7.31–7.18, (s) 1h δ6.84, (s) 1H δ5.93, (m) 1H δ2.97–2.91, (m) 1H 2.96–2.59, (m) 1H 2.53–2.45, (s) 3H δ2.09, (m) 1H δ2.0–1.90, (m) 1H δ1.63–1.53, (d) 3H δ1.24 J=7.02.

(9Z)-UAB61

¹H NMR (DMSO): (s) 1H δ12.65, (s) 1H δ10.23, (d) 2H δ7.86 J=8.64, (d) 2H δ7.72 J=8.64, (s) 1H δ7.39, (d) 1H δ7.27 J=8.12, (t) 1H δ7.17 J=7.99, (d) 1H δ6.87 J=7.97, (s) 1H δ6.02, (s) 3H δ3.78, (s) 2H δ3.34, (t) 2H δ2.63 J=6.29, (m) 3H δ2.47–2.50, (s) 3H δ2.12, (qui) 2H δ1.73 J=6.21.

(9Z)-UAB62

¹H NMR (DMSO): (s) 1H δ12.67, (s) 1H δ10.25, (d) 2H δ7.86 J=8.73, (d) 2H δ7.73 J=8.75, (s) 1H δ7.40, (d) 1H δ7.17 J=2.54, (d) 1H δ7.05 J=8.39, (dd) 1H δ6.82 J=2.52 J=5.83, (s) 3H δ3.76, (t) 2H δ2.67 J=6.11, (m) 3H δ2.56–2.50, (s) 3H δ2.12, (qui) 2H δ1.72 J=6.16.

(9Z)-UAB70

¹H NMR (DMSO): (s) 1H δ12.69, (s) 1H δ10.27, (d) 2H δ7.90 J=8.63, (d) 2H δ7.76 J=8.68, (d) 1H δ7.30 J=6.86, (m) 3H δ7.22–7.11, (s) 1H δ6.91, (s) 1H δ6.01, (s) 2H δ2.71, (s) 2H δ2.44, (s) 3H δ2.18, (s) 4H δ1.69 ¹³C NMR (CDCl₃): δ167.32, 164.64, 149.62, 145.46, 145.36, 143.90, 139.69, 130.74, 19.03, 128.67, 128.04, 127.51, 126.68, 125.15, 122.11, 118.60, UV-VIS: $\lambda_{max}$=296 nm, $\epsilon$=22527.

In conclusion, the present invention shows that substituting a fused benzyl ring for alkyl groups has little effect on the conformation on the polyene chain between C-8 and C-15, but it markedly changes the biological properties of the conformationally constrained UAB retinoids, In particular, the nuclear receptor transcriptional profiles of all-E-isomers are modified dramatically. For UAB30, this isomer displays selectively for activation of RARβ- and RARγ-mediated transcription (an RARα antagonist), whereas (all-E)-UAB8 is a potent pan-RAR agonist. The transactivational profiles of the 9Z-isomers are very similar; both 9Z-isomers of UAB8 and UAB30 are RXRα-selective compounds, with the latter displaying the most potency and selectivity. These retinoids also exhibit very different efficacies in several biological assays, and the changes in their activities correlate well with their individual transcriptional properties. For example, the high activity of (all-E)-UAB8 over (all-E)-UAB30 and (9Z)-UAB8/(9Z)-UAB30 in the prevention of skin papillomas, in the inhibition of proliferation of JMML cells is consistent with its demonstrated potent activity to activate gene expression mediated by each RAR subtype and/or its putative activity to repress gene expression of AP-1 through RAR subtypes. An exciting aspect of the present work is the higher efficacy of (all-E)- and (13Z)-UAB8 over (all-E)-RA in their ability to differentiate NB4 cells. The all-E-isomer of UAB8 is 2-fold less toxic than this isomer of RA 929), and its plasma for prolonged times. Taken together, these two UAB8 isomers and analogs may be improved agents for clinical use in the treatment of APL patients.

Further, the present invention shows that use of a potent RAR-α, all-trans-UAB8 in combination with a RXR-selective agonist, 9-cis-UAB30, significantly enhances the differentiation of NB4 cells. When compared to ATRA alone, this combination is 30-fold more effective in NB4 cell differentiation. In vivo toxicity data on all-trans-UAB8 indicates that it is less toxic than ATRA (Lin et al., 1996, *Toxicol. Appl. Pharmaco.* 139:310) and preliminary data on 9-cis-UAB30 shows that it is much less toxic than 9-cis-retinoic acid. Taken together with the enhanced stability of the UAB30 retinoids, these data suggest that improved APL therapy may be obtained when these agents are used in combination.

The following references were cited herein.

(1) Rosen, J., et al., *J. Med. Chem.* 38: 4855–4874. (1995)
(2) (a) Mangelsdorf, D. J., et al., In the Retinoids Biology, Chemistry and Medicine; 2nd ed., Raven Press: New York. pp. 319–349. (1994) (b) Gudas, L., *J. Biol. Chem.* 269: 15399–15402. (1994)
(3) Nadzan, A. M., *Annu Rev. Med. Chem.* 30:119–128. (1995)
(4) Degos, L., et al., *Blood* 85:2643–2653. (1995)
(5) Caetleberry, R. P., et al., *N. Engl. J. Med.* 331:1680–1684. (1994)
(6) Emanuel, P. D., et al., *Mol. Med. Today* 2: 468–475. (1996)
(7) Mticcio, D. D., et al., U.S. Pat. No. 5,094,783, Mar. 10, 1992.
(8) Muccio, D. D., et al., *J. Med. Chem.* 39: 3625–3635. (1996)
(9) Alam, M., et al., *J. Med. Chem.* 38: 2303–2310. (1995)
(10) Vaezi, M. F., et al., *J. Med. Chem.* 37: 4499–4507. (1994)
(11) Vaezi, M. F., et al., *Org. Prep. Proc. Int.* 19: 187–195. (1987)
(12) Hale, et al., *Labeled Compds. Radiopharm.* 13: 123–135 (1977)
(13) Zhang, X.-K., *Nature* 355: 441–446. (1992)
(14) Verma, A., et al., *Cancer Res.* 37: 2196–2201. (1977)
(15) (a) Breitman, T. R., et al., *Methods Enzymol.* 190: 118–130. (1990). (b) Tiami, M., et al., *Exp. Cell Res.* 230: 69–75. (1997)
(16) (a) Emanuel, P. D., et al., *Exp. Hematol.* 19: 1017–1024. (1991). (b) Emanuel, P. D., et al., *Blood* 77: 925–929. (1991)
(17) Lake, C. H., et al., *J. Chem. Crystallogr* 27: 231–235. (1997)
(18) (a) Sani, B. P., et al., *Biochem. J.* 171: 711–717. (1978). (b) Sani, B. P., In Chemistry and Biology of Synthetic Retinoids; Dawson, M. I., Okamuar, W. H., Eds.; CRC Press: Boca Raton, Fla., pp 365–384. (1990)
(19) Graupner, G., et al., *Nature* (London) 340: 653–656. (1989)
(20) (a) Chandraratna, R. A. S., et al., *BioMed. Chem. Lett.* 5: 523–527. (1995). (b) Nagpal, S., et al., *J. Biol. Chem.* 270: 923–927. (1995)
(21) Castleberry, R. P., et al., *Blood* 78 (Suppl. 1), 170a. (1991)
(22) (a) Lapidot, T., et al., *Blood* 82 (Suppl. 1), 197a. (1993). (b) Cambier, N., et al., *Blood* 86 (Suppl. 1), 791a. 91995)
(23) Emanuel, P. D., et al., *Blood* (Suppl. 1), 728a. (1995)
(24) (a) Yang Yen, H.-F., et al., *New Biol.* 3: 1206–1219. (1991)
(25) Salbert, G., et al., *Mol. Endocrinol.* 7: 1347–1356. (1993)
(26) (a) Fanjul, A., et al., *Nature* 372: 107–111. (1994). (b) Nagpal, S., *J. Biol. Chem.* 270: 923–927. (1995)
(27) (a) Kizaki, M., et al., *Blood* 83: 3289–3297. (1994). (b) Kizaki, M., et al., *Blood* 87: 1977–1984. (1996)
(28) Chen, J.-Y., *Nature* 382: 819–822. (1996)
(29) Lin, T.-H., et al., *Toxicol. Appl. Pharmacol.* 139: 310–316. (1996)

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A retinoid compound having a structure selected from the group consisting of:

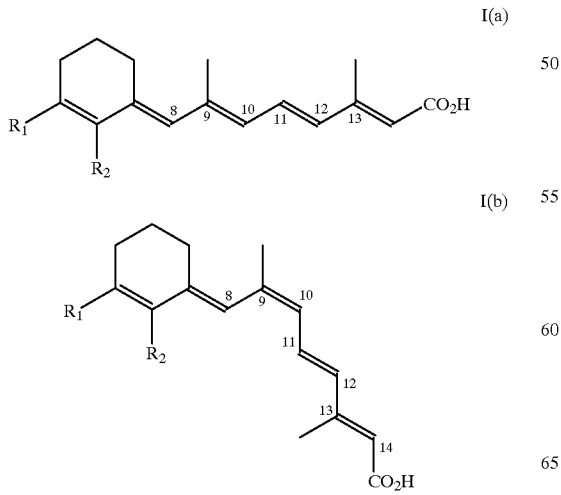

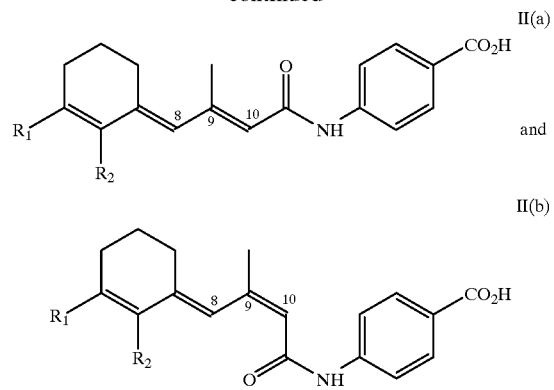

wherein when said compound has a structure selected from the group consisting of I(a) and I(b) and wherein $R_1$ is selected from the group consisting of H, ethyl, methyl, n-propyl, i-propyl, t-butyl, phenyl, benzyl, C3–C8 cyclic alkyls, aryl, and arylalkyl; $R_2$ is selected from the group consisting of cyclohexyl, 3-cyclohexenyl, benzyl, C3–C8 cyclic alkyls, and arylalkyl, wherein when said compound has a structure selected from the group consisting of I(a) and I(b) and wherein $R_2$ is 2-methylpropyl, $R_1$ is selected from the group consisting of phenyl, benzyl, C3–C8 cyclic alkyls, aryl, and arylalkyl, wherein when said compound has a structure selected from the group consisting of I(a) and I(b) and $R_2$ is n-butyl, $R_1$ is selected from the group consisting of phenyl, benzyl, C3–C8 cyclic alkyls, aryl, and arylalkyl; and wherein when said compound has a structure selected from the group consisting of II(a) and II(b), $R_1$ is selected from the group consisting of H, ethyl, methyl, n-propyl, i-propyl, t-butyl, phenyl, benzyl, C3–C8 cyclic alkyls, aryl, and arylalkyl; and $R_2$ is selected fiom the group consisting of 2-methylpropyl, n-butyl, cyclohexyl, 3-cyclohexenyl, benzyl, C3–C8 cyclic alkyls, and arylalkyl.

2. Retinoid compounds having the structure selected from the group consisting of:

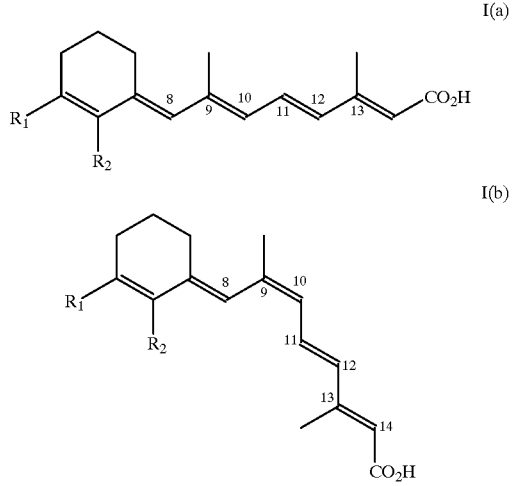

-continued

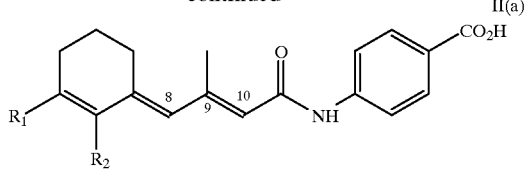
II(a)

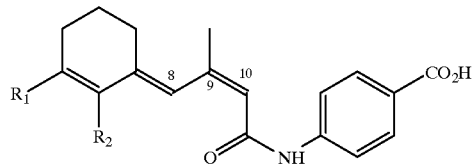
II(b)

wherein $R_1$ is selected from the group consisting of phenyl, benzyl, C3–C8 cyclic alkyls, aryl, and arylalkyl; and $R_2$ is selected from the group consisting of H, ethyl, methyl, n-propyl, and i-propyl.

3. Retinoid compounds having the structure selected from the group consisting of:

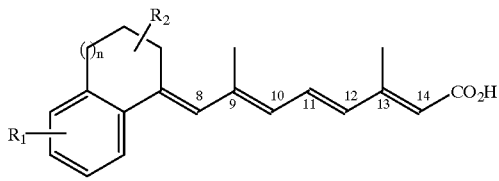
III(a)

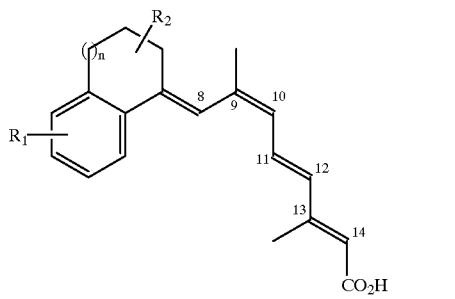
III(b)

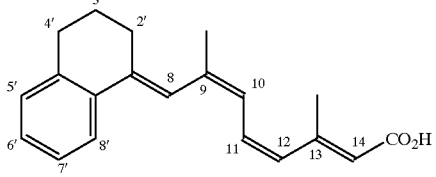
IV(a)

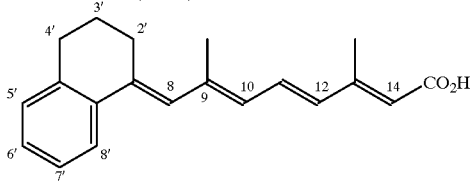
IV(b)

wherein said $R_1$ represents one or two substituents on the aryl ring and is selected from the group consisting of H, ethyl, methyl, n-propyl, i-propyl, t-butyl, phenyl, benzyl, chloro, fluoro, methoxy, ethoxy, benzyloxy, C1–C8 cyclic alkyls, aryl, arylalkyl, alkyloxy, aryloxy, arylalkyloxy, and halogen; wherein $R_2$ is selected from the group consisting of H, ethyl, methyl, n-propyl, i-propyl, 2-methylpropyl, n-butyl, cyclohexyl, 3-cyclohexenyl, benzyl, methoxy, ethoxy, benzyloxy, C1–C8 cyclic alkyls, aryl, arylalkyl, alkyloxy, aryloxy and arylalkyloxy; and wherein n=0–3.

4. A retinoid compound selected from the group consisting of (9Z)-UAB20, (all E)-UAB20, and (9Z)-UAB21, said (all E)-UAB20 has the structure:

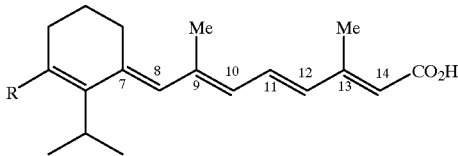

wherein said (all E)-UAB20 has a Ph group as R; and, and wherein said (9Z)-UAB20 and (9Z)-UAB21 have the structure:

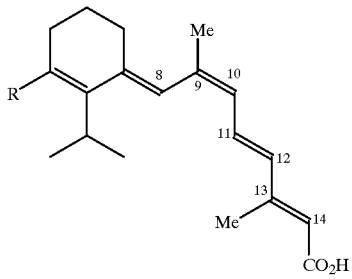

wherein said (9Z)-UAB20 has a Ph group as R and (9Z)-UAB21 has a $CH_2CH(CH_3)_2$ group as R.

5. The retinoid compounds of claim 3, wherein said compounds are selected from the group consisting of (9Z)-UAB30, (9Z)-UAB31, (9Z)-UAB32, (9Z)-UAB33, (all E)-UAB33, (9Z)-UAB34, (9Z)-UAB35, (9Z)-UAB60, (9Z)-UAB61 and (9Z)-UAB62, said (9Z)-UAB30, (9Z)-UAB31, (9Z)-UAB32, (9Z)-UAB33, (9Z)-UAB34, and (9Z)-UAB35 having the structure:

wherein said (9Z)-UAB30 has an substituent H on the aryl ring, (9Z)-UAB31 has an substituent 5'-methoxy on the aryl ring, (9Z)-UAB32 has an substituent 6'-methoxy on the aryl ring, (9Z)-UAB33 has an substituent 7'-methoxy on the aryl ring, (9Z)-UAB34 has an substituent 4'-methyl on the cycloalkyl ring; (9Z)-UAB35 has two substituents 5',7'-dimethyl on the aryl ring; wherein said (all E)-UAB33 has the structure:

wherein said (all E)-UAB33 has an substituent 7'-methoxy on the aryl ring; wherein said (9Z)-UAB60, (9Z)-UAB61 and (9Z)- UAB62 have the structure:

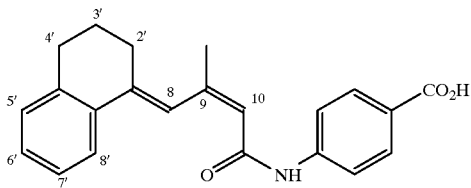

wherein said (9Z)-UAB60 has an substituent H on the aryl ring; (9Z)-UAB61 having an substituent 5'-methoxy on the aryl ring, and (9Z)-UAB62 has an substituent 7'-methoxy on the aryl ring.

6. The retinoid compounds of claim 3, wherein said compound is (9Z)-UAB40, having the structure:

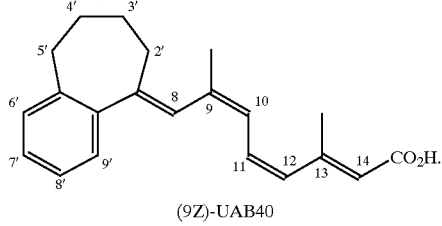

(9Z)-UAB40

7. The retinoid compounds of claim 3, wherein said compound is (9Z)-UAB70, having the structure:

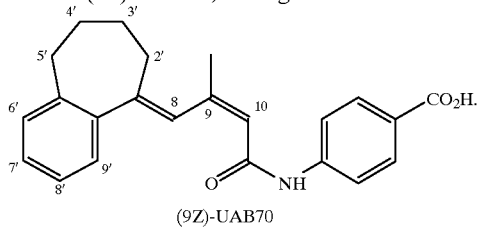

(9Z)-UAB70

8. A method of treating an individual having a neoplastic condition selected from the group consisting of brest cancer, prostate cancer, lung cancer, colon cancer, and leukemia, comprising the step of administering to said individual an effective dose of UAB8.

9. The method of claim 8, wherein said compound is combined with 4-hydroxyphenylretinamide.

10. The method of claim 8, wherein said compound is administered at a dosage range of from about 10 mg/kg of body weight to about 300 mg/kg of body weight.

11. A method of treating an individual having a neoplastic condition, comprising the step of:
administering to said individual an effective dose of the compound of claim 1.

12. The method of claim 11, wherein said compound is combined with 4-hydroxyphenylretinamide.

13. The method of claim 11, wherein said neoplastic condition is selected from the group consisting of skin cancer, breast cancer, bladder cancer, prostate cancer, lung cancer, colon cancer, and leukemia.

14. A method of reducing or preventing the occurrence of a neoplastic condition in an individual, comprising the step of administering to said individual an effective dose of the retinoid compound of claim 1.

15. The method of claim 14, wherein said neoplastic condition is selected from the group consisting of skin cancer, breast cancer, bladder cancer, prostate cancer, lung cancer, colon cancer, and leukemia.

16. The method of claim 14, wherein said compound is administered at a dosage range of from about 10 mg/kg of body weight to about 300 mg/kg of body weight.

17. A method of treating an individual having a neoplastic condition, comprising the step of: administering to said individual an effective dose of the compound of claim 2.

18. The method of claim 17, wherein said compound is combined with 4-hydroxyphenylretinamide.

19. The method of claim 17, wherein said neoplastic condition is selected from the group consisting of skin cancer, breast cancer, bladder cancer, prostate cancer, lung cancer, colon cancer, and leukemia.

20. The method of claim 17, wherein said compound is administered at a dosage range of from about 10 mg/kg of body weight to about 300 mg/kg of body weight.

21. A method of reducing or preventing the occurrence of a neoplastic condition in an individual, comprising the step of administering to said individual an effective dose of the retinoid compound of claim 2.

22. The method of claim 21, wherein said neoplastic condition is selected from the group consisting of skin cancer, breast cancer, bladder cancer, prostate cancer, lung cancer, colon cancer, and leukemia.

23. The method of claim 21, wherein said compound is administered at a dosage range of from about 10 mg/kg of body weight to about 300 mg/kg of body weight.

24. A method of treating an individual having a neoplastic condition, comprising the step of:
administering to said individual a combination of two or more retinoid compounds selected from the group consisting of UAB8/analogs and UAB30/analogs; wherein said UAB8/analogs arc selected from compounds having structures selected from the group consisting of:

I(a)

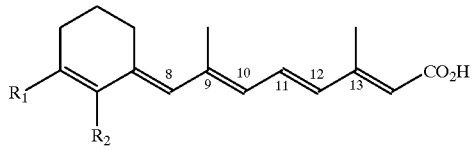

I(b)

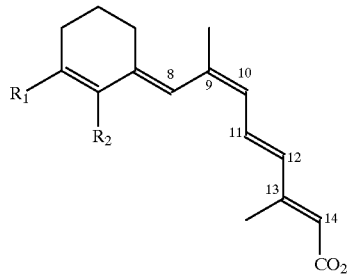

II(a)

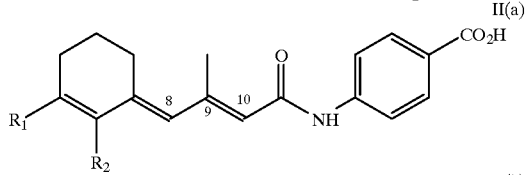

II(b)

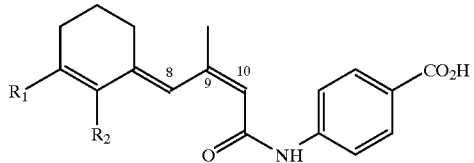

wherein when said compound has structure selected from the group consisting of I(a) and I(b), $R_1$ is selected from the group consisting of H, ethyl, methyl, n-propyl, i-propyl, t-butyl, phenyl, benzyl, C3–C8 cyclic alkyls, aryl, and arylalkyl; and, $R_2$ is selected from the group consisting of 2-methylpropyl, cyclohexyl, 3-cyclohexenyl, benzyl, C3–C8 cyclic alkyls, and arylalkyl, wherein when said compound has structure selected from the group consisting of I(a) and I(b) and $R_2$ is n-butyl, $R_1$ is selected from the group consisting of phenyl, benzyl, C3–C8 cyclic alkyls, aryl, and arylalkyl;

wherein when said compound has a structure selected from the group consisting of II(a) and II(b), $R_1$ is selected from the group consisting of H, ethyl, methyl, n-propyl, i-propyl, t-butyl, phenyl, benzyl, C3–C8 cyclic alkyls, aryl, and arylalkyl; and $R_2$ is selected from the group consisting of 2-methylpropyl, n-butyl, cyclohexyl, 3-cyclohexenyl, benzyl, C3–C8 cyclic alkyls, and arylalkyl;

wherein said UAB30/analogs are selected from compounds having the structure selected from the group consisting of:

III(a)
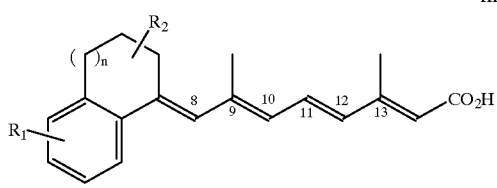

III(b)
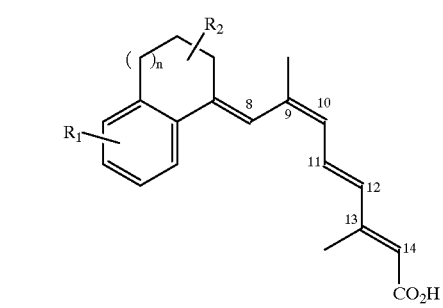

-continued

IV(a)
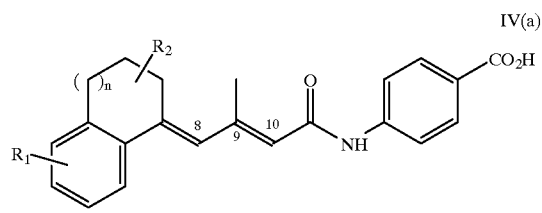

IV(b)
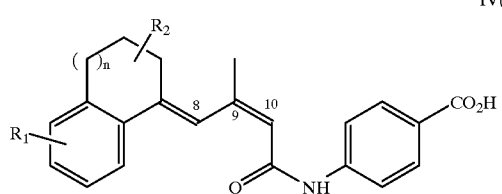

wherein said $R_1$ represents one or two substituents on the aryl ring and is selected from the group consisting of H, ethyl, methyl, n-propyl, i-propyl, t-butyl, phenyl, benzyl, chloro, fluoro, methoxy, ethoxy, benzyloxy, C1–C8 cyclic alkyls, aryl, arylalkyl, alkyloxy, aryloxy, arylalkyloxy, and halogen, $R_2$ is selected from the group consisting of H, ethyl, methyl, n-propyl, i-propyl, 2-methylpropyl, n-butyl, cyclohexyl, 3-cyclohexenyl, benzyl, methoxy, ethoxy, benzyloxy, C1–C8 cyclic alkyls, aryl, arylalkyl, alkyloxy, aryloxy and arylalkyloxy; and n=0–3.

25. The method of claim 24, wherein said neoplastic condition is selected from the group consisting of skin cancer, breast cancer, bladder cancer, prostate cancer, lung cancer, colon cancer, and leukemia.

26. The method of claim 24, wherein said combination further comprises 4-hydroxyphenylretinamide.

* * * * *

UNITED STATES PATENT AND TRADEMARK OFFICE
CERTIFICATE OF CORRECTION

PATENT NO. : 6,172,112 B1  
APPLICATION NO. : 09/287705  
DATED : January 9, 2001  
INVENTOR(S) : Brouillette et al.

Page 1 of 4

It is certified that error appears in the above-identified patent and that said Letters Patent is hereby corrected as shown below:

Figure 10: delete "UAB30" and insert in place therefor --(9Z)-UAB30--

Figure 11: delete "UAB30" and insert in place therefor --(9Z)-UAB30--

Column 1; line 26: delete "Retinoid receptors and other this" and insert in place thereof --Retinoid receptors and other members of this--

Column 2; line 15: delete "RAR-a" and insert in place thereof --RAR-α--

Column 4; line 1: delete "weight" and insert in place thereof --number--

Column 4; line 2: delete "(grams)"

Column 4; line 4: delete "UAB30" and insert in place thereof --(9Z)-UAB30--

Column 4; line 9: delete "UAB30" and insert in place thereof --(9Z)-UAB30--

Column 5; lines 1-9: delete

"
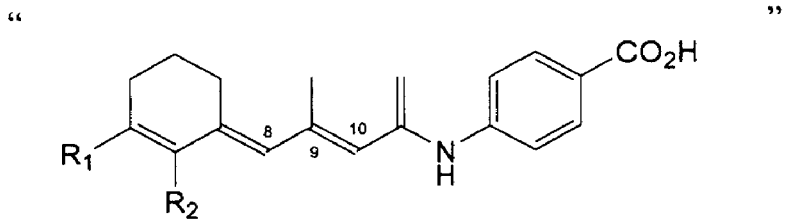
"

and insert in place thereof

--
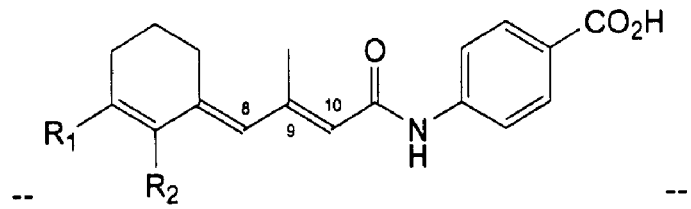
--

UNITED STATES PATENT AND TRADEMARK OFFICE
CERTIFICATE OF CORRECTION

PATENT NO.       : 6,172,112 B1
APPLICATION NO.  : 09/287705
DATED            : January 9, 2001
INVENTOR(S)      : Brouillette et al.

It is certified that error appears in the above-identified patent and that said Letters Patent is hereby corrected as shown below:

Column 9; line 9: delete "$Ch_2Cl_2$" and insert in place therefor --$CH_2Cl_2$--

Column 9; line 25: delete "ether" and insert in place therefor --either--

Column 9; line 42: delete "prepared" and insert in place thereof --purified--

Column 10; lines 9-10: delete "(2E, 4E, 6E, 8E)-8-(3′,4′-Dihydro-1′ (2′H)naphthalene-1′-ylidene)3,7-dimethyl-2,4,6-octatrienoic acid" and insert in place thereof --(2E, 4E, 6Z, 8E)-8-(3′,4′-Dihydro-1′ (2′H)naphthalene-1′-ylidene)3,7-dimethyl-2,4,6-octatrienoic acid--

Column 10; line 16: delete "(2E,4E,6E,8E)-8-(3′,4′-Dihydro-1′(2′H)-naphthalene-1′-ylidene)3,7-dimethyl-2 ,4,6-octatrienoic acid" and insert in place thereof --(2Z,4E,6E,8E)-8-(3′,4′-Dihydro-1′(2′H)-naphthalen-1′-ylidene)3,7-dimethyl-2,4,6-octatrienoic acid--

Column 13; line 26: delete "Fig. 1" and insert in place thereof --Fig. 3--

Column 14; lines 5-6: delete "Fig. 1" and insert in place thereof --Fig. 3--

Column 14; line 22: delete "(9z)-2" and insert in place thereof --(9Z)-2

Column 14; line 23: delete "(9z)- and" and insert in place thereof --(9Z)- and--

Column 14; line 25: delete "(9z)-4" and insert in place thereof --(9Z)-4--

Column 14; line 27: delete "(9z)-5$^e$" and insert in place thereof --(9Z)-5$^e$--

Column 14; line 31: delete "(9z)-UAB30$^f$" and insert in place thereof --(9Z)-UAB30$^f$--

Column 22; line 67: delete "UAB30" and insert in place thereof --(9Z)-UAB30--

UNITED STATES PATENT AND TRADEMARK OFFICE
CERTIFICATE OF CORRECTION

PATENT NO. : 6,172,112 B1
APPLICATION NO. : 09/287705
DATED : January 9, 2001
INVENTOR(S) : Brouillette et al.

It is certified that error appears in the above-identified patent and that said Letters Patent is hereby corrected as shown below:

Column 24; lines 28-34: delete

"
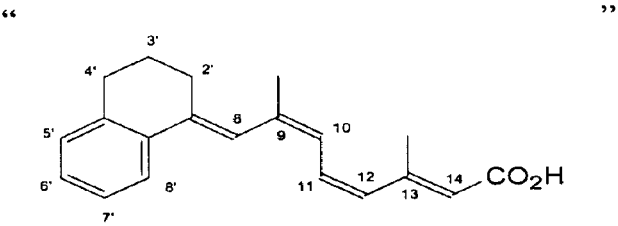
"

and insert in place thereof

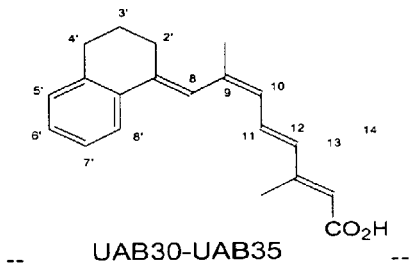

-- UAB30-UAB35 --

Column 24; lines 35-45: delete

"
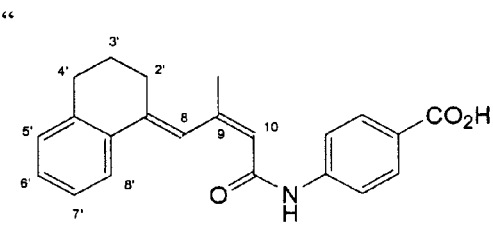
"

and insert in place thereof

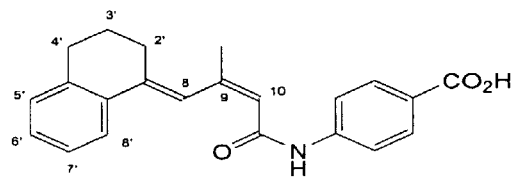

-- UAB60-UAB62 --

UNITED STATES PATENT AND TRADEMARK OFFICE
CERTIFICATE OF CORRECTION

PATENT NO.       : 6,172,112 B1
APPLICATION NO.  : 09/287705
DATED            : January 9, 2001
INVENTOR(S)      : Brouillette et al.

It is certified that error appears in the above-identified patent and that said Letters Patent is hereby corrected as shown below:

Column 24; lines 45-55: delete

"
| UAB Number | Substituent(s) | UAB Number |
|---|---|---|
| (9Z)-UAB30 | H | (9Z)-UAB60 |
| (9Z)-UAB31 | 5'-methoxy | (9Z)-UAB61 |
| (9Z)-UAB32 | 6'-methoxy | |
| (9Z)-UAB33 | 7'-methoxy | (9Z)-UAB62 |
| (all E)-UAB33 | 7'-methoxy | |
| (9Z)-UAB34 | 4'-methyl | |
| (9Z)-UAB35 | 5',7'-dimethyl | |
"

and insert in place thereof

| UAB Number | Substituent(s) | UAB Number | Substituent(s) |
|---|---|---|---|
| (9Z)-UAB30 | H | (9Z)-UAB60 | H |
| (9Z)-UAB31 | 5'-methoxy | (9Z)-UAB61 | 5'-methoxy |
| (9Z)-UAB32 | 6'-methoxy | | |
| (9Z)-UAB33 | 7'-methoxy | (9Z)-UAB62 | 7'-methoxy |
| (all E)-UAB33 | 7'-methoxy | | |
| (9Z)-UAB34 | 4'-methyl | | |
| (9Z)-UAB35 | 5',7'-dimethyl | | |

Signed and Sealed this

Fifteenth Day of January, 2008

JON W. DUDAS
*Director of the United States Patent and Trademark Office*